(12) United States Patent
Subramanian et al.

(10) Patent No.: US 9,758,385 B2
(45) Date of Patent: Sep. 12, 2017

(54) COMPOUNDS COMPRISING A HIBONITE STRUCTURE AND A METHOD FOR THEIR USE

(71) Applicant: Oregon State University, Corvallis, OR (US)

(72) Inventors: Munirpallam A. Subramanian, Philomath, OR (US); Arthur W. Sleight, Philomath, OR (US); Jun Li, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/237,993

(22) Filed: Aug. 16, 2016

(65) Prior Publication Data

US 2016/0355407 A1 Dec. 8, 2016

Related U.S. Application Data

(63) Continuation of application No. PCT/US2015/017983, filed on Feb. 27, 2015.

(60) Provisional application No. 61/946,383, filed on Feb. 28, 2014.

(51) Int. Cl.

| | |
|---|---|
| *C01B 3/40* | (2006.01) |
| *B01J 19/24* | (2006.01) |
| *C01F 7/16* | (2006.01) |
| *C01G 53/00* | (2006.01) |
| *C09C 1/00* | (2006.01) |
| *A61K 8/29* | (2006.01) |
| *C03C 1/04* | (2006.01) |
| *C08K 3/22* | (2006.01) |
| *C09D 1/00* | (2006.01) |
| *C09D 11/00* | (2014.01) |
| *C09D 17/00* | (2006.01) |

(52) U.S. Cl.
CPC ............... *C01F 7/164* (2013.01); *A61K 8/29* (2013.01); *C01G 53/006* (2013.01); *C03C 1/04* (2013.01); *C08K 3/22* (2013.01); *C09C 1/00* (2013.01); *C09C 1/0009* (2013.01); *C09D 1/00* (2013.01); *C09D 11/00* (2013.01); *C09D 17/007* (2013.01); *A61K 2800/10* (2013.01); *A61K 2800/43* (2013.01); *C01P 2002/72* (2013.01); *C01P 2002/76* (2013.01); *C01P 2002/77* (2013.01); *C01P 2002/84* (2013.01); *C01P 2006/60* (2013.01); *C08K 2003/2206* (2013.01); *C08K 2003/2227* (2013.01); *C08K 2003/2237* (2013.01); *C08K 2003/2293* (2013.01)

(58) Field of Classification Search
None
See application file for complete search history.

(56) References Cited

U.S. PATENT DOCUMENTS

| | | | |
|---|---|---|---|
| 4,906,603 | A | 3/1990 | Burgfels et al. |
| 5,894,035 | A | 4/1999 | Cinibulk et al. |
| 6,207,130 | B1 | 3/2001 | Kareiva et al. |
| 2008/0032887 | A1 | 2/2008 | Ratnasamy et al. |

FOREIGN PATENT DOCUMENTS

WO WO 2013/093819 6/2013

OTHER PUBLICATIONS

Costa et al., "Ni-doped hibonite ($CaAl_{12}O_{19}$): A new turquoise ceramic pigment," *Journal of the European Ceramic Society* 29:2671-2678, available online May 5, 2009.
Gourier et al., "X-Ray Induced Defects and Thermoluminescent Properties of Lanthanum Hexaaluminates with Magnetoplumbite-like Structure," *Journal of Solid State Chemistry* 61:67-80, 1986.
International Search Report dated Jun. 3, 2015 from International Application No. PCT/US2015/017983.
Laville et al., "Synthesis, Crystal Growth, Structural Determination, and Optical Absorption Spectroscopy of the Magnetoplumbite Type Compound $LaNiAl_{11}O_{19}$," *Journal of Solid State Chemistry* 65:301-308, 1986.
Lejus et al., "Microdurete de Monocristaux d'Hexaaluminates de Lanthanides de Type Magnetoplombite," *Materials Research Bulletin* 23(6):913-922, Jun. 1988.

*Primary Examiner* — Samantha Shterengarts
(74) *Attorney, Agent, or Firm* — Klarquist Sparkman, LLP

(57) ABSTRACT

Novel colored compounds with a hibonite structure and a method for making the same are disclosed. The compounds may have a formula $AAl_{12-x-y}M^a_xM^b_yO_{19}$ where A is typically an alkali metal, an alkaline earth metal, a rare earth metal, Pb, Bi or any combination thereof, and $M^a$ is Ni, Fe, Cu, Cr, V, Mn, or Co or any combination thereof, and $M^b$ is Ti, Sn, Ge, Si, Zr, Hf, Ga, In, Zn, Mg, Nb, Ta, Sb, Mo, W or Te or any combination thereof. Compounds with varying colors, such as blue, can be made by varying A, $M^a$ and $M^b$ and their relative amounts. Compositions comprising the compounds and methods for making and using the same are also disclosed.

25 Claims, 9 Drawing Sheets
(9 of 9 Drawing Sheet(s) Filed in Color)

FIG. 2 – Prior Art

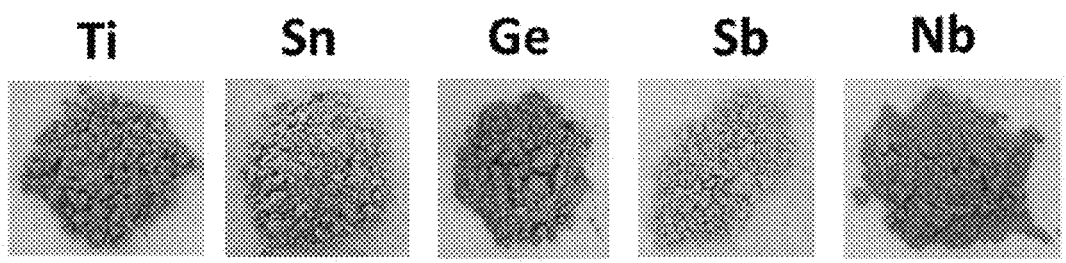
FIG. 4

COMPOUNDS COMPRISING A HIBONITE STRUCTURE AND A METHOD FOR THEIR USE

CROSS REFERENCE TO RELATED APPLICATION

This application is a continuation of International Application No. PCT/U.S.2015/017983, filed on Feb. 27, 2015, which claims the benefit of U.S. Provisional Patent Application No. 61/946,383, filed on Feb. 28, 2014, which prior applications are incorporated herein by reference in their entirety.

ACKNOWLEDGMENT OF GOVERNMENT SUPPORT

This invention was made with government support under DMR0804167 awarded by the National Science Foundation. The government has certain rights in the invention.

FIELD

This invention concerns hibonite compounds, particularly colored hibonite compounds, compositions comprising the same, and a method for making and using the compounds and compositions.

BACKGROUND

Blue inorganic pigments, such as cobalt blue ($CoAl_2O_4$), ultramarine ($Na_7Al_6Si_6O_{24}S_3$), Prussian blue ($Fe_4[Fe(CN)_6]3$), and azurite ($Cu_3(CO_3)_2(OH)_2$), are known. However, these known compounds all suffer from environmental and/or durability issues. For example, prussian blue liberates HCN under mild acidic conditions, and ultramarine and azurite are not stable with respect to heat and acidic conditions. Additionally, commercial processes for making ultramarine produce significant $SO_2$ emissions.

SUMMARY

In view of the above, there is a need for new, stable inorganic pigments comprising substantially environmentally benign and earth abundant components. Disclosed embodiments of the present application address this need and provide novel, colored compounds and a method for making and using such compounds. Certain disclosed compounds are synthesized blue hibonite compounds. In some embodiments the compounds have a formula I $$AM_{12}O_{19}$$  I.

With reference to formula I, A is selected from an alkali metal, alkaline earth metal, rare earth metal, Pb, Bi, or any combination thereof, and M is selected from Al, Fe, Ni, Ti, V, Cr, Mn, Co, Cu, Zn Ga, Ge, Si, In, Sn, Mg, Zr, Hf, Nb, Ta, Sb, Te, Mo, W, or any combination thereof. As used herein, the term metal also includes metalloids.

Also disclosed herein are compounds having a general formula II $$AAl_{12-x-y}M^a_xM^b_yO_{19}$$ 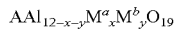 II.

With reference to formula II, A is selected from Ca, Sr, Ba, Mg, Sc, Y, La, Ce, Pr, Nd, Sm, Eu, Gd, Tb, Dy, Ho, Er, Tm, Yb, Lu, Li, Na, K, Rb, Cs, Pb, Bi or any combination thereof, $M^a$ is selected from Ni, Fe, Cu, Cr, V, Mn, or Co or any combination thereof, and $M^b$ is selected from Ti, Sn, Ge, Si, Zr, Hf, Ga, In, Zn, Mg, Nb, Ta, Sb, Mo, W or Te or any combination thereof. In some embodiments, x is from 0.01 to less than 12, y is from 0 to less than 12, x+y is less than 12, and if y is 0 then x is from 0.01 to less than 1. In other embodiments, x is from 0.01 to less than 1, y is from 0 to less than 12, and x+y is less than 12. In certain embodiments, x is from 0.01 to less than 12, y is from 0.01 to less than 12, and x+y is less than 12.

In some examples, $M^a$ comprises Fe and y is greater than 0, such as greater than or equal to 0.01 or greater than or equal to 0.1. Alternatively, $M^a$ may comprise Fe and at least one additional metal selected from Ni, Cu, Cr, V, Mn, or Co. In other examples, $M^a$ is selected from Ni, Cu, Cr, V, Mn, or Co or any combination thereof.

$M^a$ may comprise at least two metals selected from Ni, Cr, Cu, V, Mn, Co or Fe, such as V and at least one additional metal selected from Ni, Cr, Cu, Mn, Co or Fe, or Cr and at least one additional metal selected from Ni, V, Cu, Mn, Co or Fe.

In some embodiments of formula II, A is $A^1_{1-z}A^2_z$, where $A^1$ is selected from Ca, Sr, Ba, Mg, Sc, Y, Li, Na, K, Rb, Cs, Pb, Bi or any combination thereof, $A^2$ is selected from La, Ce, Pr, Nd, Sm, Eu, Gd, Tb, Dy, Ho, Er, Tm, Yb, Lu or any combination thereof, and z is from 0 to less than 1.

In any of the above embodiments, if $M^a$ is Mn and $M^b$ is Mg then x+y may be less than 1, such as less than or equal to 0.95 or less than or equal to 0.9, or x+y may be greater than 1, such as greater than or equal to 1.05 or greater than or equal to 1.1.

In some embodiments $M^a$ comprises Ni, Co or any combination thereof, and in other embodiments, $M^b$ comprises Ti. In particular embodiments A is Ca, La, Sr or any combination thereof. In some examples, x is from 0.01 to 2 and/or y is from 0 to 2 or from 0.01 to 2, and in certain examples, x+y is less than or equal to 4. Compounds having formula II may also have a hibonite crystal structure.

In some particular embodiments of formula II, $M^a$ is Co or Ni. In some particular examples, $M^b$ is selected from Ti, Ge, Sn or any combination thereof, and/or x is from 0.05 to 1.5.

In some embodiments, the compounds are chromophoric, i.e. they absorb certain wavelengths of visible light and transmit or reflect other wavelengths, and in certain embodiments they have a blue color. The blue color may have a wavelength of from about 440 nm to about 510 nm, typically from about 450 nm to about 475 nm. In any of the above embodiments, the compound may be a synthesized blue hibonite compound.

Also disclosed are embodiments of a composition comprising a disclosed compound and at least one additional component. The composition may be, for example, a paint, an ink, a dye, a glass, a plastic, an emulsion, a fabric, or a cosmetic preparation. Examples of additional composition components include, without limitation, a binder, a solvent, a catalyst, a thickener, a stabilizer, an emulsifier, a texturizer, an adhesion promoter, a UV stabilizer, a flattener, a preservative, a polymer, a dispersion aid, a plasticizer, a flame retardant, an oxide of a metal, or any combination thereof. In some embodiments where the composition is a glass, the additional component is an oxide of a metal, including, but not limited to, oxides of silicon, boron, germanium or any combination thereof. In some embodiments, the composition has a blue color, and in certain embodiments the blue color has a wavelength of from about 440 nm to about 510 nm, preferably from about 450 nm to about 475 nm. Optionally, the composition may comprise at least one additional compound disclosed herein, and this additional compound may have formula I.

Also disclosed are embodiments of a method for making disclosed compounds and compositions. One disclosed embodiment comprises selecting the metals desired in the compound, providing reactants comprising the desired metals, and combining the reactants in stoichiometric amounts to achieve a desired final ratio of the metals in the compound. The combination of reactants is then heated at an effective temperature and for an effective period of time to make the desired compound. In certain embodiments, the effective temperature is from about 1,200° C. to about 1,500° C., and the time is from greater than zero hours to about 48 hours.

In certain embodiments, the reactants comprise metal carbonates, metal oxides, metal nitrates, metal hydroxides or combinations thereof. In some embodiments the reactants are provided in a powdered form, and optionally may be pressed into a pellet before heating. The method may further comprise grinding the pellet after heating to produce a powder, pressing the powder into a pellet, and heating the pellet at a temperature of from about 1,300° C. to about 1,500° C. for from greater than zero hours to about 48 hours.

Embodiments of a method for making disclosed compositions comprise providing the compound and combining it with at least one additional component to make the composition.

Also disclosed are embodiments of a method of varying the color in a compound with formula II. In certain embodiments, the method comprises selecting metals A, $M^a$ and $M^b$ and the values of x and y to provide a desired color. Reactants are then selected comprising the desired metals, and are combined in stoichiometric amounts according to the values of x and y. The combination of reactants is heated at an effective temperature for an effective period of time to make the desired compound with the desired color.

Additionally, disclosed are embodiments of a method of using a disclosed compound, comprising providing a composition comprising the compound and applying the composition to a surface.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 provides a series of color photographs illustrating various colors of exemplary compounds with hibonite structure, having the formulae $CaAl_{12-x-y}M_xNi_yO_{19}$ (M=Ti, Sn, Ge, Sb, Nb; x,y=0.2-0.5).

DETAILED DESCRIPTION

I. Compounds
  A. Overview

The mineral known as hibonite has the ideal formula $CaAl_{12}O_{19}$. It rarely occurs naturally on Earth but has been observed frequently in meteors. As with most minerals, small amounts of other elements are found in hibonite samples. The other elements that have been reported in hibonite mineral samples are Ti, V, Cr, Mg, Si, La, Ce, Y, Sc and Th. The amounts of these trace elements are usually less than 1% and always less than 4%. It is notable that none of the many mineral samples analyzed contained detectable amounts of Ni, Cu, Zn, Ga, or In. The detection limit of these analyses is such that any amount exceeding about 0.01% would be found. Thus the compounds disclosed herein are very different than any observed in mineral samples of hibonite.

Although the color of pure $CaAl_{12}O_{19}$ hibonite is white, mineral samples are normally colored due to trace elements or defects. Observed colors are grey, dark brown, orange and blue. Attempts to correlate color with trace elements or defects have not led to a consensus.

The color of crystals is often very different from that of the powder obtained by grinding the crystals. For example, crystals of $CoAl_2O_4$ are black, but powder of the same composition and structure is a bright blue. Bright blue sapphire crystals yield a pale blue powder when ground up. Thus, it might be expected that grinding up blue hibonite crystals would produce a pale blue powder that would be of little commercial interest as a pigment.

Figure 1:
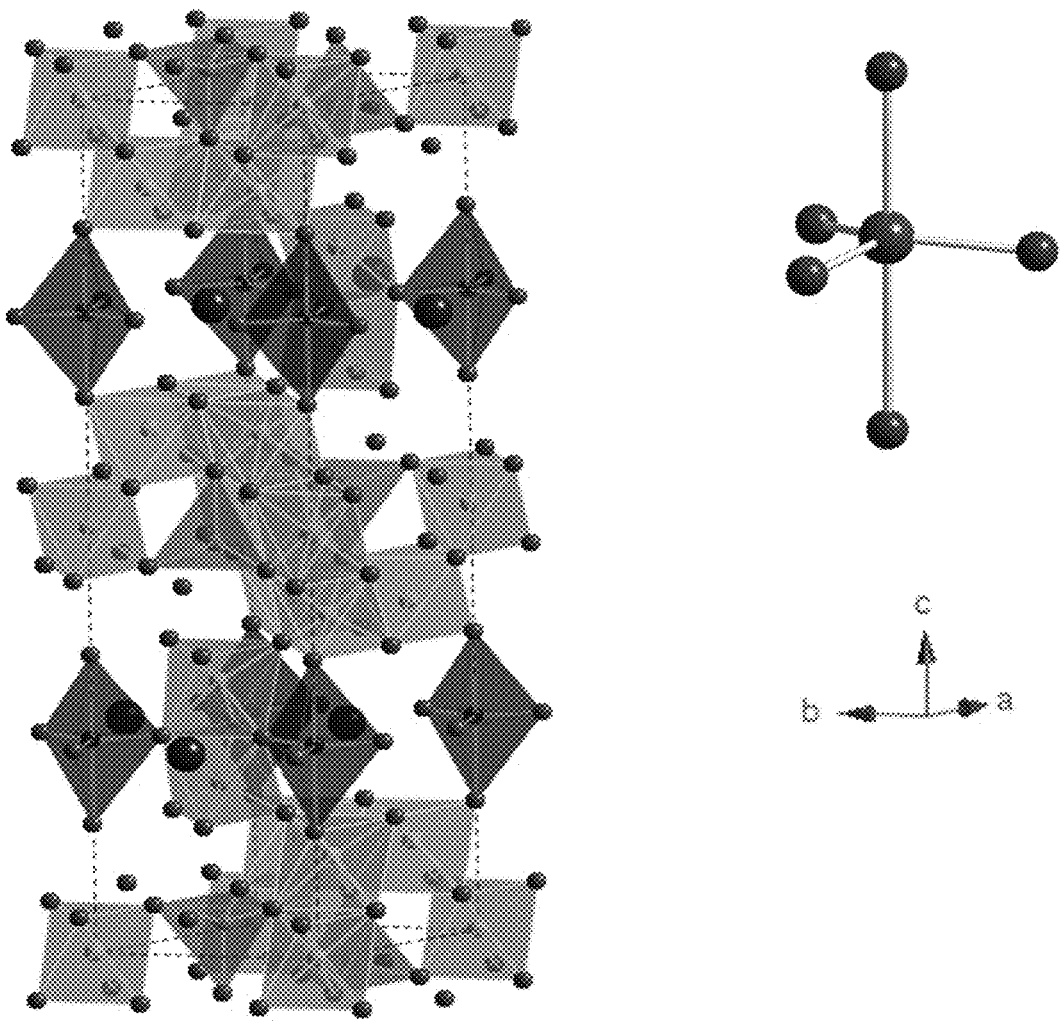
FIG. 1 provides a representation of the crystal structure of hexagonal $CaAl_{12}O_{19}$ with a hibonite structure, with Ca atoms in dark gray; oxygen atoms in red; $AlO_6$ octahedra in cyan, yellow and pink; $AlO_5$ trigonal bipyramids in dark blue; and $AlO_4$ tetrahedra in green.

Pure $CaAl_{12}O_{19}$ is white with a structure generally described in space group $P6_3/mmc$ with unit cell dimensions of a=b=5.5587 Å, c=21.8929 Å, α=β=90°, γ=120°. This hexagonal crystal structure can be viewed as two-dimensional sections perpendicular to the c axis with alternating "spinel blocks" and trigonal bipyramidal blocks (FIG. 1). Without being bound by any particular theory, it currently is believed that there are five different coordination sites for Al, including three distinct octahedra, one tetrahedron, and an unusual trigonal bipyramid connected as a corner-sharing, edge-sharing or face-sharing polyhedral network. The cation in the trigonal bipyramid polyhedron is usually displaced from the center.

The Subramanian group at Oregon State University recently discovered that a surprisingly intense bright-blue color can be obtained when $Mn^{3+}$ is introduced into the trigonal bipyramidal sites of hexagonal $YInP_3$. A range of blue colors can be obtained over much of the $YIn_{1-x}Mn_xO_3$ solid-solution by substituting Mn for In. Similar blue color is obtained when Mn3+is introduced into trigonal bipyramidal sites in other layered oxides. The resulting blue color is a consequence of both the crystal field splitting associated with the trigonal bipyramidal coordination and the short apical Mn—O bonds.

Figure 2:
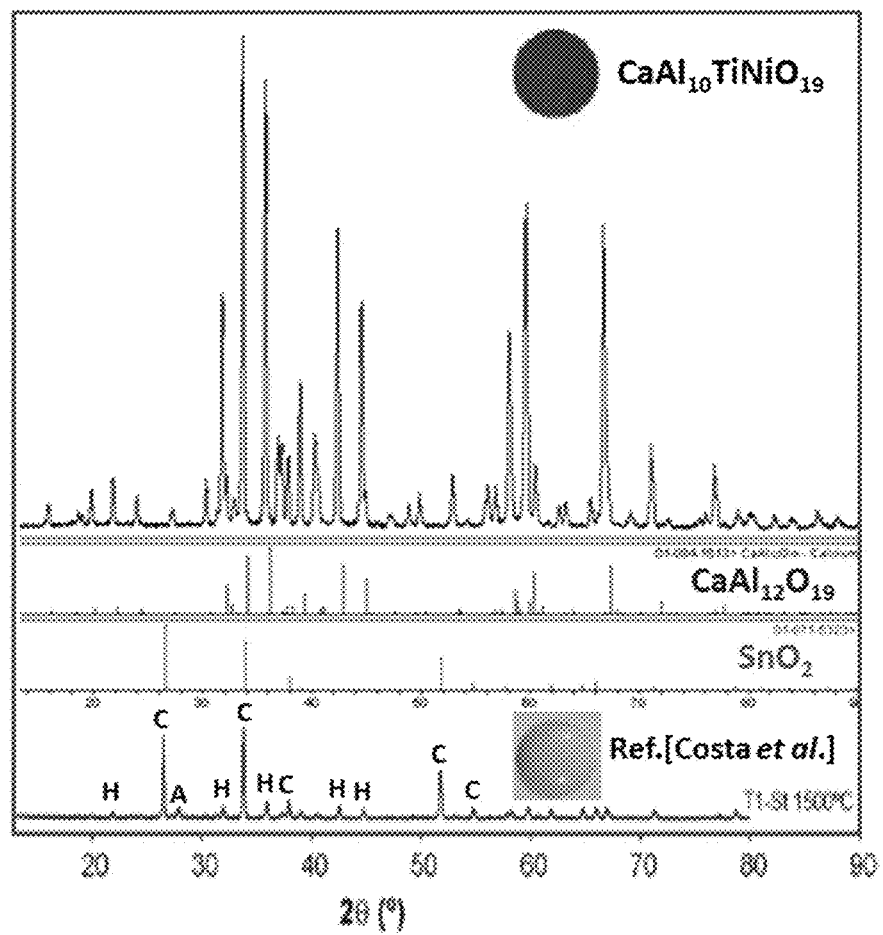
FIG. 2 provides a comparison of XRD patterns and pellet colors illustrating the difference between the pure nickel-doped hibonite phase ($CaAl_{10}TiNiO_{19}$ as an example) disclosed herein and the nickel-containing $CaAl_{12}O_{19}$ mixed phase made according to the method disclosed by Costa et al.

Costa et al. reported so-called Ni-doped hibonite as a new turquoise blue ceramic pigment, the color of which, however, is in fact only turquoise (G. Costa, et al. *Journal of the European Ceramic Society* 29 (2009) 2671-2678). Costa et al. provide no structural analysis, and the X-ray diffraction patterns displayed $SnO_2$ as the major phase with very small amount of hibonite in the mixture. FIG. 2 provides a comparison of the XRD patterns and pellet colors of the pure nickel-doped hibonite phase of $CaAl_{10}TiNiO_{19}$, as disclosed herein, and the nickel-containing $CaAl_{12}O_{19}$ mixed phase made according to the procedure disclosed by Costa et al. The top line of FIG. 2 shows an XRD pattern illustrating single phase $CaAl_{10}TiNiO_{19}$ hibonite as described herein, with a deep sky blue pellet color. The middle lines in FIG. 2 provide calculated XRD patterns for hibonite $CaAl_{12}O_{19}$ and cassiterite $SnO_2$. And the bottom line in FIG. 2 provides the XRD pattern taken from the paper by Costa et al. indicating a mixed phase with a light turquoise color: A—anorthite; C—cassiterite; H—hibonite.

Given the very small amount of hibonite detected, and the fact that $SnO_2$ is grayish white and $NiAl_2O_4$ is dark turquoise, the color of the Costa et al. material is most likely not from a hibonite phase.

B. Compounds

Disclosed herein are compounds, typically having a hibonite structure, and in certain embodiments the disclosed compounds are colored compounds. In some embodiments, the compounds have a space group $P6_3/mmc$.

The disclosed hibonite compounds typically have a general formula I $$AM_{12}O_{19} \qquad \text{I}$$

where A is selected from an alkali metal, an alkaline earth metal, a rare earth metal, Pb, Bi or any combination thereof; and M is selected from Al, Ni, Ti, V, Cr, Mn, Fe, Co, Cu, Zn Ga, Ge, Si, In, Sn, Mg, Zr, Hf, Nb, Ta, Sb, Te, Mo, W or combinations thereof. In other embodiments, A is selected from Ca, Sr, Ba, Mg, Sc, Y, La, Ce, Pr, Nd, Sm, Eu, Gd, Tb, Dy, Ho, Er, Tm, Yb, Lu, Li, Na, K, Rb, Cs, Pb, Bi or any combination thereof. In some embodiments, M comprises Al, one or more metals selected from Ni, Cr, Cu, V, Mn, Fe, or Co, and optionally one or more metals selected from Ti, Sn, Ge, Si, Zr, Hf, Ga, In, Zn, Mg, Nb, Ta, Sb, Mo, W or Te.

Also disclosed herein are compounds having a general formula II $$AAl_{12-x-y}M^a{}_xM^b{}_yO_{19} \qquad \text{II.}$$

With reference to formula II, A is selected from an alkali metal, alkaline earth metal, rare earth metal, Pb, Bi or any combination thereof; $M^a$ is selected from Ni, Fe, Cu, Cr, V, Mn, or Co or any combination thereof; $M^b$ is selected from Ti, Sn, Ge, Si, Zr, Hf, Ga, In, Zn, Mg, Nb, Ta, Sb, Mo, W or Te or any combination thereof. Typically, A is selected from Ca, Sr, Ba, Mg, Sc, Y, La, Ce, Pr, Nd, Sm, Eu, Gd, Tb, Dy, Ho, Er, Tm, Yb, Lu, Li, Na, K, Rb, Cs, Pb, Bi or any combination thereof. In some embodiments, x is from 0.01 to less than 12, y is from 0 to less than 12, x+y is less than 12, and if y is 0 then x is from 0.01 to less than 1. In other embodiments, x is from 0.01 to less than 1, y is from 0 to less than 12, and x+y is less than 12. In certain embodiments, x is from 0.01 to less than 12, y is from 0.01 to less than 12, and x+y is less than 12.

In some examples, A is $A^1{}_{1-z}A^2{}_z$, and $A^1$ is selected from Ca, Sr, Ba, Mg, Sc, Y, Li, Na, K, Rb, Cs, Pb, Bi or any combination thereof; $A^2$ is selected from La, Ce, Pr, Nd, Sm, Eu, Gd, Tb, Dy, Ho, Er, Tm, Yb, Lu or any combination thereof; and z is from 0 to less than 1, such as from 0 to 0.98, 0 to 0.95, or 0 to 0.9.

In some embodiments, $M^a$ comprises Fe and y is greater than 0, such as greater than or equal to 0.01 or greater than or equal to 0.1, and in some other embodiments, $M^a$ comprises Fe and at least one additional metal selected from Ni, Cu, Cr, V, Mn, or Co. In other embodiments, $M^a$ is selected from Ni, Cu, Cr, V, Mn, or Co or any combination thereof.

In any of the above embodiments, if $M^a$ is Mn and $M^b$ is Mg, then x+y may be less than 1, such as less than or equal to 0.95 or less than or equal to 0.9, or x+y may be greater than 1, such as greater than or equal to 1.05 or greater than or equal to 1.1.

In some embodiments, y is from greater than 0 to less than 12, such as from 0.01 to less than 12, or from 0.1 to less than 12. In other embodiments, $M^a$ comprises at least two metals selected from Ni, Cr, Cu, V, Mn, Co, Fe. In some examples, $M^a$ comprises V and at least one additional metal selected from Ni, Cu, Cr, Fe, Mn, or Co. In other examples, $M^a$ comprises Cr and at least one additional metal selected from Ni, Cu, Fe, V, Mn, or Co.

In some examples, x+y is less or equal to 4, and in other examples, x is from about 0.01 to about 2, and/or y is from 0 to about 2 or y is from about 0.01 to about 2.

While not being bound to any particular theory, is it believed that $M^a$ cations are chromophores, i.e. they are the part of the compound that is responsible for the color, and that $M^b$ cations can be used to enhance the color and/or for charge balance.

In certain embodiments, $M^a$ comprises Ni, La, Co or any combination thereof. In some particular embodiments of formula II, $M^a$ is Co or Ni. In some embodiments, x is from 0.05 to 1.5 and/or $M^b$ is selected from Ti, Ge, Sn or any combination thereof.

In some working embodiments, exemplary compounds were prepared where $M^a$ comprised Ni or Co. Other compounds were prepared such that $M^b$ comprised Ti. In certain working embodiments, A comprised Ca, Sr, La, Ce, Pr, Nd, Y, Sc, K, Na, Rb, Mg, Ba, Yb or combinations thereof. In some working embodiments, A was Ca and Sr, Sr and La, Ca and La, Ca and Y, Ca and Ce, Ca and Pr, Ca and Na, Ca and K, Ca and Rb, Ca and Cs, Ca and Mg, Ca and Ba, Sr and Y, Sr and Ce, Sr and Nd, Sr and Pr, Ca and Sc, Ca and Yb, or Ca and Nd. In other working embodiments, A was Ca, Sr, Ce, La, Pr or Nd, and in particular working embodiments A comprised Ca, La, Sr or any combination thereof.

Exemplary compounds according to the present invention are selected from $CaAl_{11.8}Ni_{0.2}O_{19}$, $CaAl_{11.5}Ni_{0.5}O_{19}$, $CaAl_{11}Sn_{0.5}Ni_{0.5}O_{19}$, $CaAl_{10}SnNiO_{19}$, $CaAl_{11}Zn_{0.5}Ni_{0.5}O_{19}$, $CaAl_{11}Ge_{0.5}Ni_{0.5}O_{19}$, $CaAl_{10}GeNiO_{19}$, $CaAl_{11}Ga_{0.5}Ni_{0.5}O_{19}$, $CaAl_{11}Ti_{0.5}Ni_{0.5}O_{19}$, $CaAl_{10}Ti_{0.5}Si_{0.5}NiO_{19}$, $CaAl_{10}Ti_{0.5}Ge_{0.5}NiO_{19}$, $CaAl_{10}Ti_{0.5}Sn_{0.5}NiO_{19}$, $CaAl_8TiSnNi_2O_{19}$, $CaAl_{10}TiNi_{0.5}Cu_{0.5}O_{19}$, $CaAl_{10}TiNi_{0.5}Cr_{0.5}O_{19}$, $CaAl_{10}TiNi_{0.5}Zn_{0.5}O_{19}$, $CaAl_{11.8}Ti_{0.1}Ni_{0.1}O_{19}$, $CaAl_{11.6}Ti_{0.2}Ni_{0.2}O_{19}$, $CaAl_{11.4}Ti_{0.3}Ni_{0.3}O_{19}$, $CaAl_{11.2}Ti_{0.4}Ni_{0.4}O_{19}$, $CaAl_{11}Ti_{0.5}Ni_{0.5}O_{19}$, $CaAl_{10.8}Ti_{0.6}Ni_{0.6}O_{19}$, $CaAl_{10.6}Ti_{0.7}Ni_{0.7}O_{19}$, $CaAl_{10.4}Ti_{0.8}Ni_{0.8}O_{19}$, $CaAl_{10.2}$ $Ti_{0.9}Ni_{0.9}O_{19}$, $CaAl_{10}TiNiO_{19}$, $CaAl_{9.6}Ti_{1.2}Ni_{1.2}O_{19}$, $CaAl_8Ti_2Ni_2O_{19}$, $Ca_{0.8}Sr_{0.2}Al_{11.6}Ti_{0.2}Ni_{0.2}O_{19}$, $Ca_{0.6}Sr_{0.4}Al_{11.2}Ti_{0.4}Ni_{0.4}O_{19}$, $Ca_{0.4}Sr_{0.6}Al_{10.8}Ti_{0.6}Ni_{0.6}O_{19}$, $Ca_{0.2}Sr_{0.8}Al_{10.4}Ti_{0.8}Ni_{0.8}O_{19}$, $SrAl_{10}TiNiO_{19}$, $SrAl_{9.6}Ti_{1.2}Ni_{1.2}O_{19}$, $SrAl_{11}Ti_{0.5}Ni_{0.5}O_{19}$, $SrAl_8Ti_2Ni_2O_{19}$, $Ca_{0.5}Sr_{0.5}Al_8Ti_2Ni_2O_{19}$, $Ca_{0.5}Sr_{0.5}Al_{10}TiNiO_{19}$, $Ca_{0.5}Sr_{0.5}Al_{10}GeNiO_{19}$, $Ca_{0.5}Sr_{0.5}Al_{11}Sn_{0.5}Ni_{0.5}O_{19}$, $Ca_{0.5}Sr_{0.5}Al_{10}SnNiO_{19}$, $Sr_{0.9}La_{0.1}Al_{11.9}Ni_{0.1}O_{19}$, $Sr_{0.8}La_{0.2}Al_{11.8}Ni_{0.2}O_{19}$, $Sr_{0.7}La_{0.3}Al_{11.7}Ni_{0.3}O_{19}$, $Sr_{0.6}La_{0.4}Al_{11.6}Ni_{0.4}O_{19}$, $Sr_{0.5}La_{0.5}Al_{11.5}Ni_{0.5}O_{19}$, $Sr_{0.4}La_{0.6}Al_{11.4}Ni_{0.6}O_{19}$, $Sr_{0.3}La_{0.7}Al_{11.3}Ni_{0.7}O_{19}$, $Sr_{0.2}La_{0.8}Al_{11.2}Ni_{0.8}O_{19}$, $Sr_{0.1}La_{0.9}Al_{11.1}Ni_{0.9}O_{19}$, $Ca_{0.9}La_{0.1}Al_{11.9}Ni_{0.1}O_{19}$, $Ca_{0.8}La_{0.2}Al_{11.8}Ni_{0.2}O_{19}$, $Ca_{0.7}La_{0.3}Al_{11.7}Ni_{0.3}O_{19}$, $Ca_{0.6}La_{0.4}Al_{11.6}Ni_{0.4}O_{19}$, $Ca_{0.5}La_{0.5}Al_{11.5}Ni_{0.5}O_{19}$, $Ca_{0.4}La_{0.6}Al_{11.4}Ni_{0.6}O_{19}$, $Ca_{0.3}La_{0.7}Al_{11.3}Ni_{0.7}O_{19}$, $Ca_{0.2}La_{0.8}Al_{11.2}Ni_{0.8}O_{19}$, $Ca_{0.1}La_{0.9}Al_{11.1}Ni_{0.9}O_{19}$, $LaAl_{11}NiO_{19}$, $Ca_{0.75}La_{0.25}Al_{11.25}Ti_{0.25}Ni_{0.5}O_{19}$, $Ca_{0.5}La_{0.5}Al_{11}Ti_{0.25}Ni_{0.75}O_{19}$, $Ca_{0.5}La_{0.5}Al_{10.5}Ti_{0.5}NiO_{19}$, $Ca_{0.25}La_{0.75}Al_{9.75}Ti_{0.75}Ni_{1.5}O_{19}$, $Ca_{0.5}La_{0.5}Al_{8.5}Ti_{1.5}Ni_2O_{19}$, $LaAl_9TiNi_2O_{19}$, $Ca_{0.5}La_{0.5}Al_{11}In_{0.5}Ni_{0.5}O_{19}$, $Ca_{0.5}La_{0.5}Al_{11}Ga_{0.5}Ni_{0.5}O_{19}$, $Ca_{0.5}La_{0.5}Al_{11}Ge_{0.25}Ni_{0.75}O_{19}$, $Ca_{0.5}La_{0.5}Al_{11}Sn_{0.25}Ni_{0.75}O_{19}$, $Ca_{0.75}La_{0.25}Al_{11.75}Ni_{0.25}O_{19}$, $Ca_{0.5}Y_{0.5}Al_{11}Ti_{0.25}Ni_{0.75}O_{19}$, $Ca_{0.5}Ce_{0.5}Al_{11}Ti_{0.25}Ni_{0.75}O_{19}$, $Ca_{0.5}Pr_{0.5}Al_{11}Ti_{0.25}Ni_{0.75}O_{19}$, $Ca_{0.5}Na_{0.5}Al_{10.5}TiNi_{0.5}O_{19}$, $Ca_{0.5}K_{0.5}Al_{10.5}TiNi_{0.5}O_{19}$, $Ca_{0.5}Rb_{0.5}Al_{10.5}TiNi_{0.5}O_{19}$, $Ca_{0.5}Cs_{0.5}Al_{10.5}TiNi_{0.5}O_{19}$, $Ca_{0.8}Mg_{0.2}Al_{11.6}Ti_{0.2}Ni_{0.2}O_{19}$, $Ca_{0.5}Ba_{0.5}Al_8Ti_2Ni_2O_{19}$, $Sr_{0.9}Y_{0.1}Al_{11.9}Ni_{0.1}O_{19}$, $Sr_{0.8}Y_{0.2}Al_{11.8}Ni_{0.2}O_{19}$, $Sr_{0.8}Ce_{0.2}Al_{11.8}Ni_{0.2}O_{19}$, $Sr_{0.8}Nd_{0.2}Al_{11.8}Ni_{0.2}O_{19}$, $Sr_{0.8}Pr_{0.2}Al_{11.8}Ni_{0.2}O_{19}$, $Ca_{0.9}Y_{0.1}Al_{11.9}Ni_{0.1}O_{19}$, $Ca_{0.8}Y_{0.2}Al_{11.8}Ni_{0.2}O_{19}$, $Ca_{0.7}Y_{0.3}Al_{11.7}Ni_{0.3}O_{19}$, $Ca_{0.6}Y_{0.4}Al_{11.6}Ni_{0.4}O_{19}$, $Ca_{0.5}La_{0.5}Al_{10.5}Zn_{0.5}Sn_{0.5}Ni_{0.5}O_{19}$, $Ca_{0.5}La_{0.5}Al_{10.5}Cu_{0.5}Sn_{0.5}Ni_{0.5}O_{19}$, $Ca_{0.8}Sc_{0.2}Al_{11.8}Ni_{0.2}O_{19}$, $Ca_{0.8}Yb_{0.2}Al_{11.8}Ni_{0.2}O_{19}$, $Ca_{0.7}Sr_{0.3}Al_{11.5}Ni_{0.5}O_{19}$, $CaAl_7Ti_{1.5}Ge_{0.5}MgNi_2O_{19}$, $Ca_{0.9}Ce_{0.1}Al_{11.9}Ni_{0.1}O_{19}$, $Ca_{0.8}Ce_{0.2}Al_{11.8}Ni_{0.2}O_{19}$, $Ca_{0.7}Ce_{0.3}Al_{11.7}Ni_{0.3}O_{19}$, $Ca_{0.6}Ce_{0.4}Al_{11.6}Ni_{0.4}O_{19}$, $Ca_{0.5}Ce_{0.5}Al_{11.5}Ni_{0.5}O_{19}$, $Ca_{0.4}Ce_{0.6}Al_{11.4}Ni_{0.6}O_{19}$, $Ca_{0.3}Ce_{0.7}Al_{11.3}Ni_{0.7}O_{19}$, $Ca_{0.2}Ce_{0.8}Al_{11.2}Ni_{0.8}O_{19}$, $Ca_{0.1}Ce_{0.9}Al_{11.1}Ni_{0.9}O_{19}$, $CeAl_{11}NiO_{19}$, $Ca_{0.9}Pr_{0.1}Al_{11.9}Ni_{0.1}O_{19}$, $Ca_{0.8}Pr_{0.2}Al_{11.8}Ni_{0.2}O_{19}$, $Ca_{0.7}Pr_{0.3}Al_{11.7}Ni_{0.3}O_{19}$, $Ca_{0.6}Pr_{0.4}Al_{11.6}Ni_{0.4}O_{19}$, $Ca_{0.5}Pr_{0.5}Al_{11.5}Ni_{0.5}O_{19}$, $Ca_{0.4}Pr_{0.6}Al_{11.4}Ni_{0.6}O_{19}$, $Ca_{0.3}Pr_{0.7}Al_{11.3}Ni_{0.7}O_{19}$, $Ca_{0.2}Pr_{0.8}Al_{11.2}Ni_{0.8}O_{19}$, $Ca_{0.1}Pr_{0.9}Al_{11.1}Ni_{0.9}O_{19}$, $PrAl_{11}NiO_{19}$, $Ca_{0.9}Nd_{0.1}Al_{11.9}Ni_{0.1}O_{19}$, $Ca_{0.8}Nd_{0.2}Al_{11.8}Ni_{0.2}O_{19}$, $Ca_{0.7}Nd_{0.3}Al_{11.7}Ni_{0.3}O_{19}$, $Ca_{0.6}Nd_{0.4}Al_{11.6}Ni_{0.4}O_{19}$, $Ca_{0.5}Nd_{0.5}Al_{11.5}Ni_{0.5}O_{19}$, $Ca_{0.4}Nd_{0.6}Al_{11.4}Ni_{0.6}O_{19}$, $Ca_{0.3}Nd_{0.7}Al_{11.3}Ni_{0.7}O_{19}$, $Ca_{0.2}Nd_{0.8}Al_{11.2}Ni_{0.8}O_{19}$, $Ca_{0.1}Nd_{0.9}Al_{11.1}Ni_{0.9}O_{19}$, $NdAl_{11}NiO_{19}$, $CaAl_{11.4}Nb_{0.2}Ni_{0.4}O_{19}$, $CaAl_{11.4}Ta_{0.2}Ni_{0.4}O_{19}$, $CaAl_{11.4}V_{0.2}Ni_{0.4}O_{19}$, $CaAl_{11.4}Sb_{0.2}Ni_{0.4}O_{19}$, $CaAl_{11}Zr_{0.5}Ni_{0.5}O_{19}$ or $CaAl_{11}Te_{0.5}Ni_{0.5}O_{19}$.

In any of the above embodiments the compounds may have a hibonite crystal structure, and in any of the above embodiments the compounds may be chromophoric. In some embodiments, the compounds are blue. In particular embodiments, disclosed compounds have a blue color with a wavelength of from about 440 nm to about 510 nm, preferably from about 450 nm to about 475 nm. In certain working embodiments, compounds where $M^a$ comprised Ni had a blue color.

II. Method of Making Compounds

A general method for making the compounds disclosed herein comprises providing a mixture of reactants selected to produce a desired compound and heating the reactants.

The compounds can be made in different forms, such as powders and pellets. To make pellets of the disclosed compounds, the metals desired in the final compounds are selected. Reactants are then combined in stoichiometric amounts to achieve the desired final ratio of the metals in the compound. Reactants suitable to make the disclosed compounds include elemental metals, and compounds that comprise the desired metals, including, but not limited to, oxides, carbonates, nitrates, nitrites, nitrides, azides, sulfates, sulfites, halides such as chloride, bromide, iodide or fluoride, phosphates, hydroxides, hydrates, or any combination thereof. In some embodiments, the reactants are either metal oxides, or compounds that decompose to provide metal oxides. In working embodiments, the alkali metals and alkaline earth metals were typically provided as metal carbonate salts, and the other metals were typically provided as metal oxides. In some embodiments, the reactants are ground to a powder, either before, during or after mixing, and optionally formed into a pellet.

The combination of reactants is then heated at an effective temperature for an effective period of time to form the desired compound. In some embodiments, the temperature is from about 800° C. to about 2,000° C., typically from about 1,100° C. to about 1,700° C., and even more typically from about 1,200° C. to about 1,500° C. The effective period of time is from greater than zero hours up to at least 72 hours, typically from about 4 hours to about 60 hours, and more typically from about 10 hours to about 48 hours. In some embodiments, reactants are heated at an effective temperature in the presence of air. A person of ordinary skill in the art will appreciate that, if atmospheric oxygen is not required to produce desired compounds, reactants can be heated in an inert atmosphere. A person of ordinary skill in the art also will appreciate that a pressure effective to produce the desired compounds could be about atmospheric pressure or less than atmospheric pressure, such as from less than 1 mm Hg to about 760 mmHg, preferably from about 10 mm Hg to about 700 mm Hg. Or the pressure could be greater than atmospheric pressure, such as from about 1 atmosphere pressure to greater than 10 atmospheres, preferably from about 1.1 atmospheres to about 5 atmospheres pressure.

After heating, the compounds are characterized by X-ray diffraction. If the X-ray diffraction indicates that the compound is impure, i.e. it is not a single phase, the compound is ground into a powder, re-pelletized and reheated. The reheating temperature could be substantially the same as the initial heating temperature, or it could be higher or lower than the initial heating temperature. The pellet is typically reheated for from about 2 to about 48 hours. The grinding, re-pelletizing and reheating is repeated until the X-ray diffraction indicates a pure compound, i.e. a single phase. In certain working embodiments, the combination of reactants was heated at about 1,300° C. for about 12 hours, then ground to a powder, re-pelletized and reheated at from about 1,300° C. to about 1,500° C. for about 12 hours. To make powders of the disclosed compound, the pellets are ground after the final heating step.

Exemplary compounds made according to the disclosed method are characterized by X-ray diffraction, diffuse reflectance spectroscopy and magnetic susceptibility. Table 1, below, lists exemplary compounds and information regarding their color, starting materials and reaction conditions.

TABLE 1

Composition, color and structures of exemplary compounds

| Composition | Color | Starting Materials | Heating Temperatures and Times |
|---|---|---|---|
| $CaAl_{12}O_{19}$ | white | $CaCO_3$, $Al_2O_3$ | $1^{st}$: 1300° C., 12 hr; $2^{nd}$: 1500° C., 12 hr |
| $CaAl_{11.8}Mn_{0.2}O_{19}$ | tan/burlywood | $CaCO_3$, $Al_2O_3$, $Mn_2O_3$ | $1^{st}$: 1300° C., 12 hr; $2^{nd}$: 1450° C., 12 hr |
| $CaAl_{11.5}Mn_{0.5}O_{19}$ | gray | $CaCO_3$, $Al_2O_3$, $Mn_2O_3$ | $1^{st}$: 1300° C., 12 hr; $2^{nd}$: 1450° C., 12 hr |
| $CaAl_{11.8}Ni_{0.2}O_{19}$ | pale turquoise | $CaCO_3$, $Al_2O_3$, NiO | $1^{st}$: 1300° C., 12 hr; $2^{nd}$: 1450° C., 12 hr |
| $CaAl_{11.5}Ni_{0.5}O_{19}$ | light sky blue | $CaCO_3$, $Al_2O_3$, NiO | $1^{st}$: 1300° C., 12 hr; $2^{nd}$: 1450° C., 12 hr |
| $CaAl_{11.8}Co_{0.2}O_{19}$ | light purplish blue | $CaCO_3$, $Al_2O_3$, $Co_3O_4$ | $1^{st}$: 1300° C., 12 hr; $2^{nd}$: 1450° C., 12 hr |
| $CaAl_{11.8}Ti_{0.2}O_{19}$ | white | $CaCO_3$, $Al_2O_3$, $TiO_2$ | $1^{st}$: 1300° C., 12 hr; $2^{nd}$: 1450° C., 12 hr |
| $CaAl_{11.8}Cr_{0.2}O_{19}$ | light pink | $CaCO_3$, $Al_2O_3$, $Cr_2O_3$ | $1^{st}$: 1300° C., 12 hr; $2^{nd}$: 1450° C., 12 hr |
| $CaAl_{11.8}V_{0.2}O_{19}$ | mint cream | $CaCO_3$, $Al_2O_3$, $V_2O_5$ | $1^{st}$: 1300° C., 12 hr; $2^{nd}$: 1450° C., 12 hr |
| $CaAl_{11.8}Cu_{0.2}O_{19}$ | misty rose | $CaCO_3$, $Al_2O_3$, CuO | $1^{st}$: 1300° C., 12 hr; $2^{nd}$: 1450° C., 12 hr |
| $CaAl_{11}Sn_{0.5}Mn_{0.5}O_{19}$ | light pink | $CaCO_3$, $Al_2O_3$, $SnO_2$, $Mn_2O_3$ | $1^{st}$: 1300° C., 12 hr; $2^{nd}$: 1450° C., 12 hr |
| $CaAl_{11}Sn_{0.5}Ni_{0.5}O_{19}$ | sky blue | $CaCO_3$, $Al_2O_3$, $SnO_2$, NiO | $1^{st}$: 1300° C., 12 hr; $2^{nd}$: 1450° C., 12 hr |
| $CaAl_{10}SnNiO_{19}$ | deep sky blue | $CaCO_3$, $Al_2O_3$, $SnO_2$, NiO | $1^{st}$: 1300° C., 12 hr; $2^{nd}$: 1400° C., 12 hr |
| $CaAl_{11}Sn_{0.5}Fe_{0.5}O_{19}$ | light greenish beige | $CaCO_3$, $Al_2O_3$, $SnO_2$, $Fe_2O_3$ | $1^{st}$: 1300° C., 12 hr; $2^{nd}$: 1450° C., 12 hr |
| $CaAl_{11}Sn_{0.5}Cu_{0.5}O_{19}$ | White | $CaCO_3$, $Al_2O_3$, $SnO_2$, CuO | $1^{st}$: 1300° C., 12 hr; $2^{nd}$: 1450° C., 12 hr |
| $CaAl_{11}Sn_{0.5}Cr_{0.5}O_{19}$ | light pink | $CaCO_3$, $Al_2O_3$, $SnO_2$, $Cr_2O_3$ | $1^{st}$: 1300° C., 12 hr; $2^{nd}$: 1450° C., 12 hr |
| $CaAl_{11}Zn_{0.5}Ni_{0.5}O_{19}$ | light blue | $CaCO_3$, $Al_2O_3$, ZnO, NiO | $1^{st}$: 1300° C., 12 hr; $2^{nd}$: 1450° C., 12 hr |
| $CaAl_{11}Ge_{0.5}Ni_{0.5}O_{19}$ | sky blue | $CaCO_3$, $Al_2O_3$, $GeO_2$, NiO | $1^{st}$: 1300° C., 12 hr; $2^{nd}$: 1450° C., 12 hr |
| $CaAl_{10}GeNiO_{19}$ | deep sky blue | $CaCO_3$, $Al_2O_3$, $GeO_2$, NiO | $1^{st}$: 1300° C., 12 hr; $2^{nd}$: 1400° C., 12 hr |
| $CaAl_{11}Ga_{0.5}Ni_{0.5}O_{19}$ | light turquoise | $CaCO_3$, $Al_2O_3$, $Ga_2O_3$, NiO | $1^{st}$: 1300° C., 12 hr; $2^{nd}$: 1450° C., 12 hr |
| $CaAl_{11}Ti_{0.5}Ni_{0.5}O_{19}$ | deep sky blue | $CaCO_3$, $Al_2O_3$, $TiO_2$, NiO | $1^{st}$: 1300° C., 12 hr; $2^{nd}$: 1450° C., 12 hr |
| $CaAl_{11}Ti_{0.5}Cu_{0.5}O_{19}$ | ivory | $CaCO_3$, $Al_2O_3$, $TiO_2$, CuO | $1^{st}$: 1300° C., 12 hr; $2^{nd}$: 1450° C., 12 hr |
| $CaAl_{11}Ti_{0.5}Fe_{0.5}O_{19}$ | light dark khaki | $CaCO_3$, $Al_2O_3$, $TiO_2$, $Fe_2O_3$ | $1^{st}$: 1300° C., 12 hr; $2^{nd}$: 1450° C., 12 hr |
| $CaAl_{11}Ti_{0.5}Mn_{0.5}O_{19}$ | very light pink | $CaCO_3$, $Al_2O_3$, $TiO_2$, $Mn_2O_3$ | $1^{st}$: 1300° C., 12 hr; $2^{nd}$: 1450° C., 12 hr |
| $CaAl_{10}Ti_{0.5}Si_{0.5}NiO_{19}$ | sky blue | $CaCO_3$, $Al_2O_3$, $TiO_2$, $SiO_2$, NiO | $1^{st}$: 1300° C., 12 hr; $2^{nd}$: 1450° C., 12 hr |
| $CaAl_{10}Ti_{0.5}Ge_{0.5}NiO_{19}$ | royal blue | $CaCO_3$, $Al_2O_3$, $TiO_2$, $GeO_2$, NiO | $1^{st}$: 1300° C., 12 hr; $2^{nd}$: 1450° C., 12 hr |
| $CaAl_{10}Ti_{0.5}Sn_{0.5}NiO_{19}$ | deep sky blue | $CaCO_3$, $Al_2O_3$, $TiO_2$, $SnO_2$, NiO | $1^{st}$: 1300° C., 12 hr; $2^{nd}$: 1450° C., 12 hr |
| $CaAl_8TiSnNi_2O_{19}$ | dark turquoise/cyan | $CaCO_3$, $Al_2O_3$, $TiO_2$, $SnO_2$, NiO | $1^{st}$: 1300° C., 12 hr; $2^{nd}$: 1350° C., 12 hr |
| $CaAl_{10}TiNi_{0.5}Cu_{0.5}O_{19}$ | dark slate gray | $CaCO_3$, $Al_2O_3$, $TiO_2$, CuO, NiO | $1^{st}$: 1300° C., 12 hr; $2^{nd}$: 1450° C., 12 hr |
| $CaAl_{10}TiNi_{0.5}Cr_{0.5}O_{19}$ | dark turquoise | $CaCO_3$, $Al_2O_3$, $TiO_2$, $Cr_2O_3$ | $1^{st}$: 1300° C., 12 hr; $2^{nd}$: 1450° C., 12 hr |
| $CaAl_{10}TiNi_{0.5}Zn_{0.5}O_{19}$ | deep sky blue | $CaCO_3$, $Al_2O_3$, $TiO_2$, CuO, NiO | $1^{st}$: 1300° C., 12 hr; $2^{nd}$: 1450° C., 12 hr |
| $CaAl_{11.8}Ti_{0.1}Ni_{0.1}O_{19}$ | light sky blue | $CaCO_3$, $Al_2O_3$, $TiO_2$, NiO | $1^{st}$: 1300° C., 12 hr; $2^{nd}$: 1450° C., 12 hr |
| $CaAl_{11.6}Ti_{0.2}Ni_{0.2}O_{19}$ | sky blue | $CaCO_3$, $Al_2O_3$, $TiO_2$, NiO | $1^{st}$: 1300° C., 12 hr; $2^{nd}$: 1450° C., 12 hr |
| $CaAl_{11.4}Ti_{0.3}Ni_{0.3}O_{19}$ | sky blue | $CaCO_3$, $Al_2O_3$, $TiO_2$, NiO | $1^{st}$: 1300° C., 12 hr; $2^{nd}$: 1450° C., 12 hr |
| $CaAl_{11.2}Ti_{0.4}Ni_{0.4}O_{19}$ | deep sky blue | $CaCO_3$, $Al_2O_3$, $TiO_2$, NiO | $1^{st}$: 1300° C., 12 hr; $2^{nd}$: 1400° C., 12 hr |
| $CaAl_{11}Ti_{0.5}Ni_{0.5}O_{19}$ | deep sky blue | $CaCO_3$, $Al_2O_3$, $TiO_2$, NiO | $1^{st}$: 1300° C., 12 hr; $2^{nd}$: 1400° C., 12 hr |
| $CaAl_{10.8}Ti_{0.6}Ni_{0.6}O_{19}$ | dark sky blue | $CaCO_3$, $Al_2O_3$, $TiO_2$, NiO | $1^{st}$: 1300° C., 12 hr; $2^{nd}$: 1350° C., 12 hr |

TABLE 1-continued

Composition, color and structures of exemplary compounds

| Composition | Color | Starting Materials | Heating Temperatures and Times |
|---|---|---|---|
| $CaAl_{10.6}Ti_{0.7}Ni_{0.7}O_{19}$ | dodger blue | $CaCO_3$, $Al_2O_3$, $TiO_2$, NiO | $1^{st}$: 1300° C., 12 hr; $2^{nd}$: 1350° C., 12 hr |
| $CaAl_{10.4}Ti_{0.8}Ni_{0.8}O_{19}$ | dodger blue | $CaCO_3$, $Al_2O_3$, $TiO_2$, NiO | $1^{st}$: 1300° C., 12 hr; $2^{nd}$: 1300° C., 12 hr |
| $CaAl_{10.2}Ti_{0.9}Ni_{0.9}O_{19}$ | dodger blue | $CaCO_3$, $Al_2O_3$, $TiO_2$, NiO | $1^{st}$: 1300° C., 12 hr; $2^{nd}$: 1300° C., 12 hr |
| $CaAl_{10}TiNiO_{19}$ | deep sky blue | $CaCO_3$, $Al_2O_3$, $TiO_2$, NiO | $1^{st}$: 1300° C., 12 hr; $2^{nd}$: 1300° C., 12 hr |
| $CaAl_{9.6}Ti_{1.2}Ni_{1.2}O_{19}$ | royal blue | $CaCO_3$, $Al_2O_3$, $TiO_2$, NiO | $1^{st}$: 1300° C., 12 hr; $2^{nd}$: 1300° C., 12 hr |
| $CaAl_8Ti_2Ni_2O_{19}$ | dark sky blue | $CaCO_3$, $Al_2O_3$, $TiO_2$, NiO | $1^{st}$: 1300° C., 12 hr; $2^{nd}$: 1300° C., 12 hr |
| $CaAl_{11}Ge_{0.5}Mn_{0.5}O_{19}$ | light salmon | $CaCO_3$, $Al_2O_3$, $GeO_2$, MnO | $1^{st}$: 1300° C., 12 hr; $2^{nd}$: 1400° C., 12 hr |
| $CaAl_{11}In_{0.5}Mn_{0.5}O_{19}$ | saddle brown | $CaCO_3$, $Al_2O_3$, $In_2O_3$, $Mn_2O_3$ | $1^{st}$: 1300° C., 12 hr; $2^{nd}$: 1400° C., 12 hr |
| $CaAl_{11}Sn_{0.5}Mn_{0.5}O_{19}$ | light pink | $CaCO_3$, $Al_2O_3$, $SnO_2$, MnO | $1^{st}$: 1300° C., 12 hr; $2^{nd}$: 1400° C., 12 hr |
| $CaAl_{11}Ti_{0.5}Mn_{0.5}O_{19}$ | tan | $CaCO_3$, $Al_2O_3$, $TiO_2$, MnO | $1^{st}$: 1300° C., 12 hr; $2^{nd}$: 1400° C., 12 hr |
| $Ca_{0.8}Sr_{0.2}Al_{11.6}Ti_{0.2}Ni_{0.2}O_{19}$ | light sky blue | $CaCO_3$, $SrCO_3$, $Al_2O_3$, $TiO_2$, NiO | $1^{st}$: 1300° C., 12 hr; $2^{nd}$: 1400° C., 12 hr |
| $Ca_{0.6}Sr_{0.4}Al_{11.2}Ti_{0.4}Ni_{0.4}O_{19}$ | sky blue | $CaCO_3$, $SrCO_3$, $Al_2O_3$, $TiO_2$, NiO | $1^{st}$: 1300° C., 12 hr; $2^{nd}$: 1400° C., 12 hr |
| $Ca_{0.4}Sr_{0.6}Al_{10.8}Ti_{0.6}Ni_{0.6}O_{19}$ | darker sky blue | $CaCO_3$, $SrCO_3$, $Al_2O_3$, $TiO_2$, NiO | $1^{st}$: 1300° C., 12 hr; $2^{nd}$: 1400° C., 12 hr |
| $Ca_{0.2}Sr_{0.8}Al_{10.4}Ti_{0.6}Ni_{0.8}O_{19}$ | darker sky blue | $CaCO_3$, $SrCO_3$, $Al_2O_3$, $TiO_2$, NiO | $1^{st}$: 1300° C., 12 hr; $2^{nd}$: 1400° C., 12 hr |
| $SrAl_{10}TiNiO_{19}$ | deep sky blue | $SrCO_3$, $Al_2O_3$, $TiO_2$, NiO | $1^{st}$: 1300° C., 12 hr; $2^{nd}$: 1300° C., 12 hr |
| $SrAl_{9.6}Ti_{1.2}Ni_{1.2}O_{19}$ | deep sky blue | $SrCO_3$, $Al_2O_3$, $TiO_2$, NiO | $1^{st}$: 1300° C., 12 hr; $2^{nd}$: 1300° C., 12 hr |
| $SrAl_{11}Ti_{0.5}Ni_{0.5}O_{19}$ | light blue | $SrCO_3$, $Al_2O_3$, $TiO_2$, NiO | $1^{st}$: 1300° C., 12 hr; $2^{nd}$: 1400° C., 12 hr |
| $SrAl_8Ti_2Ni_2O_{19}$ | dark turquoise/cyan | $SrCO_3$, $Al_2O_3$, $TiO_2$, NiO | $1^{st}$: 1300° C., 12 hr; $2^{nd}$: 1300° C., 12 hr |
| $Ca_{0.5}Sr_{0.5}Al_8Ti_2Ni_2O_{19}$ | dark turquoise | $CaCO_3$, $SrCO_3$, $Al_2O_3$, $TiO_2$, NiO | $1^{st}$: 1300° C., 12 hr; $2^{nd}$: 1300° C., 12 hr |
| $Ca_{0.5}Sr_{0.5}Al_{10}TiNiO_{19}$ | dodger blue | CaCO, $SrCO_3$, $Al_2O_3$, $TiO_2$, NiO | $1^{st}$: 1300° C., 12 hr; $2^{nd}$: 1300° C., 12 hr |
| $Ca_{0.5}Sr_{0.5}Al_{10}GeNiO_{19}$ | deep sky blue | $CaCO_3$, $SrCO_3$, $Al_2O_3$, $GeO_2$, NiO | $1^{st}$: 1300° C., 12 hr; $2^{nd}$: 1300° C., 12 hr |
| $Ca_{0.5}Sr_{0.5}Al_{11}Sn_{0.5}Ni_{0.5}O_{19}$ | sky blue (bright) | $CaCO_3$, $SrCO_3$, $Al_2O_3$, $SnO_2$, NiO | $1^{st}$: 1300° C., 12 hr; $2^{nd}$: 1400° C., 12 hr |
| $Ca_{0.5}Sr_{0.5}Al_{10}SnNiO_{19}$ | deep sky blue | $CaCO_3$, $SrCO_3$, $Al_2O_3$, $SnO_2$, NiO | $1^{st}$: 1300° C., 12 hr; $2^{nd}$: 1300° C., 12 hr |
| $Sr_{0.9}La_{0.1}Al_{11.9}Ni_{0.1}O_{19}$ | Light Sky Blue | $SrCO_3$, $La_2O_3$, $Al_2O_3$, NiO | $1^{st}$: 1300° C., 12 hr; $2^{nd}$: 1450° C., 12 hr |
| $Sr_{0.8}La_{0.2}Al_{11.8}Ni_{0.2}O_{19}$ | Sky Blue | $SrCO_3$, $La_2O_3$, $Al_2O_3$, NiO | $1^{st}$: 1300° C., 12 hr; $2^{nd}$: 1450° C., 12 hr |
| $Sr_{0.7}La_{0.3}Al_{11.7}Ni_{0.3}O_{19}$ | Sky Blue | $SrCO_3$, $La_2O_3$, $Al_2O_3$, NiO | $1^{st}$: 1300° C., 12 hr; $2^{nd}$: 1450° C., 12 hr |
| $Sr_{0.6}La_{0.4}Al_{11.6}Ni_{0.4}O_{19}$ | Sky Blue | $SrCO_3$, $La_2O_3$, $Al_2O_3$, NiO | $1^{st}$: 1300° C., 12 hr; $2^{nd}$: 1450° C., 12 hr |
| $Sr_{0.5}La_{0.5}Al_{11.5}Ni_{0.5}O_{19}$ | Sky Blue | $SrCO_3$, $La_2O_3$, $Al_2O_3$, NiO | $1^{st}$: 1300° C., 12 hr; $2^{nd}$: 1400° C., 12 hr |
| $Sr_{0.4}La_{0.6}Al_{11.4}Ni_{0.6}O_{19}$ | Sky Blue | $SrCO_3$, $La_2O_3$, $Al_2O_3$, NiO | $1^{st}$: 1300° C., 12 hr; $2^{nd}$: 1400° C., 12 hr |
| $Sr_{0.3}La_{0.7}Al_{11.3}Ni_{0.7}O_{19}$ | Sky Blue | $SrCO_3$, $La_2O_3$, $Al_2O_3$, NiO | $1^{st}$: 1300° C., 12 hr; $2^{nd}$: 1350° C., 12 hr |
| $Sr_{0.2}La_{0.8}Al_{11.2}Ni_{0.8}O_{19}$ | Sky Blue | $SrCO_3$, $La_2O_3$, $Al_2O_3$, NiO | $1^{st}$: 1300° C., 12 hr; $2^{nd}$: 1350° C., 12 hr |
| $Sr_{0.1}La_{0.9}Al_{11.1}Ni_{0.9}O_{19}$ | Sky Blue | $SrCO_3$, $La_2O_3$, $Al_2O_3$, NiO | $1^{st}$: 1300° C., 12 hr; $2^{nd}$: 1300° C., 12 hr |
| $SrAl_{12}O_{19}$ | white | $SrCO_3$, $Al_2O_3$ | $1^{st}$: 1300° C., 12 hr; $2^{nd}$: 1500° C., 12 hr |
| $Ca_{0.9}La_{0.1}Al_{11.9}Ni_{0.1}O_{19}$ | Light Sky Blue | $CaCO_3$, $La_2O_3$, $Al_2O_3$, NiO | $1^{st}$: 1300° C., 12 hr; $2^{nd}$: 1450° C., 12 hr |
| $Ca_{0.8}La_{0.2}Al_{11.8}Ni_{0.2}O_{19}$ | Sky Blue | $CaCO_3$, $La_2O_3$, $Al_2O_3$, NiO | $1^{st}$: 1300° C., 12 hr; $2^{nd}$: 1450° C., 12 hr |
| $Ca_{0.7}La_{0.3}Al_{11.7}Ni_{0.3}O_{19}$ | Sky Blue | $CaCO_3$, $La_2O_3$, $Al_2O_3$, NiO | $1^{st}$: 1300° C., 12 hr; $2^{nd}$: 1450° C., 12 hr |
| $Ca_{0.6}La_{0.4}Al_{11.6}Ni_{0.4}O_{19}$ | Sky Blue | $CaCO_3$, $La_2O_3$, $Al_2O_3$, NiO | $1^{st}$: 1300° C., 12 hr; $2^{nd}$: 1450° C., 12 hr |

TABLE 1-continued

Composition, color and structures of exemplary compounds

| Composition | Color | Starting Materials | Heating Temperatures and Times |
|---|---|---|---|
| $Ca_{0.5}La_{0.5}Al_{11.5}Ni_{0.5}O_{19}$ | Sky Blue | $CaCO_3$, $La_2O_3$, $Al_2O_3$, NiO | $1^{st}$: 1300° C., 12 hr; $2^{nd}$: 1400° C., 12 hr |
| $Ca_{0.4}La_{0.6}Al_{11.4}Ni_{0.6}O_{19}$ | Sky Blue | $CaCO_3$, $La_2O_3$, $Al_2O_3$, NiO | $1^{st}$: 1300° C., 12 hr; $2^{nd}$: 1400° C., 12 hr |
| $Ca_{0.3}La_{0.7}Al_{11.3}Ni_{0.7}O_{19}$ | Sky Blue | $CaCO_3$, $La_2O_3$, $Al_2O_3$, NiO | $1^{st}$: 1300° C., 12 hr; $2^{nd}$: 1350° C., 12 hr |
| $Ca_{0.2}La_{0.8}Al_{11.2}Ni_{0.8}O_{19}$ | Sky Blue | $CaCO_3$, $La_2O_3$, $Al_2O_3$, NiO | $1^{st}$: 1300° C., 12 hr; $2^{nd}$: 1350° C., 12 hr |
| $Ca_{0.1}La_{0.9}Al_{11.1}Ni_{0.9}O_{19}$ | Sky Blue | $CaCO_3$, $La_2O_3$, $Al_2O_3$, NiO | $1^{st}$: 1300° C., 12 hr; $2^{nd}$: 1300° C., 12 hr |
| $LaAl_{11}NiO_{19}$ | Sky Blue | $La_2O_3$, $Al_2O_3$, NiO | $1^{st}$: 1300° C., 12 hr; $2^{nd}$: 1300° C., 12 hr |
| $Ca_{0.75}La_{0.25}Al_{11.25}Ti_{0.25}Ni_{0.5}O_{19}$ | deep sky blue | $CaCO_3$, $La_2O_3$, $Al_2O_3$, $TiO_2$, NiO | $1^{st}$: 1300° C., 12 hr; $2^{nd}$: 1400° C., 12 hr |
| $Ca_{0.5}La_{0.5}Al_{11}Ti_{0.25}Ni_{0.75}O_{19}$ | deep sky blue (brighter) | $CaCO_3$, $La_2O_3$, $Al_2O_3$, $TiO_2$, NiO | $1^{st}$: 1300° C., 12 hr; $2^{nd}$: 1350° C., 12 hr |
| $Ca_{0.5}La_{0.5}Al_{10.5}Ti_{0.5}NiO_{19}$ | royal blue (darker) | $CaCO_3$, $La_2O_3$, $Al_2O_3$, $TiO_2$, NiO | $1^{st}$: 1300° C., 12 hr; $2^{nd}$: 1450° C., 12 hr |
| $Ca_{0.25}La_{0.75}Al_{9.75}Ti_{0.75}Ni_{1.5}O_{19}$ | royal blue (darkest) | $CaCO_3$, $La_2O_3$, $Al_2O_3$, $TiO_2$, NiO | $1^{st}$: 1300° C., 12 hr; $2^{nd}$: 1300° C., 12 hr |
| $Ca_{0.5}La_{0.5}Al_{8.5}Ti_{1.5}Ni_2O_{19}$ | dark turquoise | $CaCO_3$, $La_2O_3$, $Al_2O_3$, $TiO_2$, NiO | $1^{st}$: 1300° C., 12 hr; $2^{nd}$: 1300° C., 12 hr |
| $LaAl_9TiNi_2O_{19}$ | dark turquoise | $La_2O_3$, $Al_2O_3$, $TiO_2$, NiO | $1^{st}$: 1300° C., 12 hr; $2^{nd}$: 1300° C., 12 hr |
| $Ca_{0.5}La_{0.5}Al_{11}In_{0.5}Ni_{0.5}O_{19}$ | light cyan | $CaCO_3$, $La_2O_3$, $Al_2O_3$, $In_2O_3$, NiO | $1^{st}$: 1300° C., 12 hr; $2^{nd}$: 1400° C., 12 hr |
| $Ca_{0.5}La_{0.5}Al_{11}Ga_{0.5}Ni_{0.5}O_{19}$ | light cyan | $CaCO_3$, $La_2O_3$, $Al_2O_3$, $Ga_2O_3$, NiO | $1^{st}$: 1300° C., 12 hr; $2^{nd}$: 1400° C., 12 hr |
| $Ca_{0.5}La_{0.5}Al_{11}Ge_{0.25}Ni_{0.75}O_{19}$ | deep sky blue | $CaCO_3$, $La_2O_3$, $Al_2O_3$, $GeO_2$, NiO | $1^{st}$: 1300° C., 12 hr; $2^{nd}$: 1350° C., 12 hr |
| $Ca_{0.5}La_{0.5}Al_{11}Sn_{0.25}Ni_{0.75}O_{19}$ | deep sky blue | $CaCO_3$, $La_2O_3$, $Al_2O_3$, $SnO_2$, NiO | $1^{st}$: 1300° C., 12 hr; $2^{nd}$: 1350° C., 12 hr |
| $Ca_{0.75}La_{0.25}Al_{11.75}Ni_{0.25}O_{19}$ | Sky Blue | $CaCO_3$, $La_2O_3$, $Al_2O_3$, NiO | $1^{st}$: 1300° C., 12 hr; $2^{nd}$: 1450° C., 12 hr |
| $Ca_{0.5}Y_{0.5}Al_{11}Ti_{0.25}Ni_{0.75}O_{19}$ | turquoise | $CaCO_3$, $Y_2O_3$, $Al_2O_3$, $TiO_2$, NiO | $1^{st}$: 1300° C., 12 hr; $2^{nd}$: 1350° C., 12 hr |
| $Ca_{0.5}Ce_{0.5}Al_{11}Ti_{0.25}Ni_{0.75}O_{19}$ | deep sky blue | $CaCO_3$, $CeO_2$, $Al_2O_3$, $TiO_2$, NiO | $1^{st}$: 1300° C., 12 hr; $2^{nd}$: 1350° C., 12 hr |
| $Ca_{0.5}Pr_{0.5}Al_{11}Ti_{0.25}Ni_{0.75}O_{19}$ | deep sky blue | $CaCO_3$, $Pr_6O_{11}$, $Al_2O_3$, $TiO_2$, NiO | $1^{st}$: 1300° C., 12 hr; $2^{nd}$: 1350° C., 12 hr |
| $Ca_{0.5}Na_{0.5}Al_{10.5}TiNi_{0.5}O_{19}$ | bright royal blue | $CaCO_3$, $Na_2CO_3$, $Al_2O_3$, $TiO_2$, NiO | $1^{st}$: 1300° C., 12 hr; $2^{nd}$: 1400° C., 12 hr |
| $Ca_{0.5}K_{0.5}Al_{10.5}TiNi_{0.5}O_{19}$ | deep sky blue | $CaCO_3$, $K_2CO_3$, $Al_2O_3$, $TiO_2$, NiO | $1^{st}$: 1300° C., 12 hr; $2^{nd}$: 1400° C., 12 hr |
| $Ca_{0.5}Rb_{0.5}Al_{10.5}TiNi_{0.5}O_{19}$ | royal blue | $CaCO_3$, $Rb_2CO_3$, $Al_2O_3$, $TiO_2$, NiO | $1^{st}$: 1300° C., 12 hr; $2^{nd}$: 1400° C., 12 hr |
| $Ca_{0.5}Cs_{0.5}Al_{10.5}TiNi_{0.5}O_{19}$ | deep sky blue | $CaCO_3$, $Cs_2CO_3$, $Al_2O_3$, $TiO_2$, NiO | $1^{st}$: 1300° C., 12 hr; $2^{nd}$: 1400° C., 12 hr |
| $Ca_{0.8}Mg_{0.2}Al_{11.6}Ti_{0.2}Ni_{0.2}O_{19}$ | light sky blue | $CaCO_3$, MgO, $Al_2O_3$, $TiO_2$, NiO | $1^{st}$: 1300° C., 12 hr; $2^{nd}$: 1450° C., 12 hr |
| $Ca_{0.5}Ba_{0.5}Al_8Ti_2Ni_2O_{19}$ | dark turquoise | $CaCO_3$, $BaCO_3$, $Al_2O_3$, $TiO_2$, NiO | $1^{st}$: 1300° C., 12 hr; $2^{nd}$: 1300° C., 12 hr |
| $Sr_{0.9}Y_{0.1}Al_{11.9}Ni_{0.1}O_{19}$ | light sky blue | $SrCO_3$, $Y_2O_3$, $Al_2O_3$, NiO | $1^{st}$: 1300° C., 12 hr; $2^{nd}$: 1450° C., 12 hr |
| $Sr_{0.8}Y_{0.2}Al_{11.8}Ni_{0.2}O_{19}$ | sky blue | $SrCO_3$, $Y_2O_3$, $Al_2O_3$, NiO | $1^{st}$: 1300° C., 12 hr; $2^{nd}$: 1450° C., 12 hr |
| $Sr_{0.8}Ce_{0.2}Al_{11.8}Ni_{0.2}O_{19}$ | sky blue | $SrCO_3$, $CeO_4$, $Al_2O_3$, NiO | $1^{st}$: 1300° C., 12 hr; $2^{nd}$: 1450° C., 12 hr |
| $Sr_{0.8}Nd_{0.2}Al_{11.8}Ni_{0.2}O_{19}$ | sky blue | $SrCO_3$, $Nd_2O_3$, $Al_2O_3$, NiO | $1^{st}$: 1300° C., 12 hr; $2^{nd}$: 1450° C., 12 hr |
| $Sr_{0.8}Pr_{0.2}Al_{11.8}Ni_{0.2}O_{19}$ | sky blue | $SrCO_3$, $Pr_6O_{11}$, $Al_2O_3$, NiO | $1^{st}$: 1300° C., 12 hr; $2^{nd}$: 1450° C., 12 hr |
| $Ca_{0.9}Y_{0.1}Al_{11.9}Ni_{0.1}O_{19}$ | Light Sky Blue | $CaCO_3$, $Y_2O_3$, $Al_2O_3$, NiO | $1^{st}$: 1300° C., 12 hr; $2^{nd}$: 1450° C., 12 hr |
| $Ca_{0.8}Y_{0.2}Al_{11.8}Ni_{0.2}O_{19}$ | Sky Blue | $CaCO_3$, $Y_2O_3$, $Al_2O_3$, NiO | $1^{st}$: 1300° C., 12 hr; $2^{nd}$: 1450° C., 12 hr |
| $Ca_{0.7}Y_{0.3}Al_{11.7}Ni_{0.3}O_{19}$ | Sky Blue | $CaCO_3$, $Y_2O_3$, $Al_2O_3$, NiO | $1^{st}$: 1300° C., 12 hr; $2^{nd}$: 1450° C., 12 hr |
| $Ca_{0.6}Y_{0.4}Al_{11.6}Ni_{0.4}O_{19}$ | Sky Blue | $CaCO_3$, $Y_2O_3$, $Al_2O_3$, NiO | $1^{st}$: 1300° C., 12 hr; $2^{nd}$: 1400° C., 12 hr |
| $Ca_{0.5}La_{0.5}Al_{10.5}Zn_{0.5}Sn_{0.5}Ni_{0.5}O_{19}$ | Dark bluish turquoise | $CaCO_3$, $La_2O_3$, $Al_2O_3$, ZnO, $SnO_2$, NiO | $1^{st}$: 1300° C., 12 hr; $2^{nd}$: 1400° C., 12 hr |

TABLE 1-continued

Composition, color and structures of exemplary compounds

| Composition | Color | Starting Materials | Heating Temperatures and Times |
|---|---|---|---|
| $Ca_{0.5}La_{0.5}Al_{10.5}Cu_{0.5}Sn_{0.5}Ni_{0.5}O_{19}$ | deep sky blue | $CaCO_3$, $La_2O_3$, $Al_2O_3$, CuO, $SnO_2$, NiO | $1^{st}$: 1300° C., 12 hr; $2^{nd}$: 1400° C., 12 hr |
| $Ca_{0.8}Sc_{0.2}Al_{11.8}Ni_{0.2}O_{19}$ | light blue | $CaCO_3$, $Sc_2O_3$, $Al_2O_3$, NiO | $1^{st}$: 1300° C., 12 hr; $2^{nd}$: 1450° C., 12 hr |
| $Ca_{0.8}Yb_{0.2}Al_{11.8}Ni_{0.5}O_{19}$ | light blue | $CaCO_3$, $Yb_2O_3$, $Al_2O_3$, NiO | $1^{st}$: 1300° C., 12 hr; $2^{nd}$: 1450° C., 12 hr |
| $Ca_{0.7}Sr_{0.3}Al_{11.5}Ni_{0.5}O_{19}$ | light turquoise | $CaCO_3$, $SrCO_3$, $Al_2O_3$, NiO | $1^{st}$: 1300° C., 12 hr; $2^{nd}$: 1400° C., 12 hr |
| $CaAl_7Ti_{1.5}Ge_{0.5}MgNi_2O_{19}$ | sky blue | $CaCO_3$, $Al_2O_3$, $TiO_2$, $GeO_2$, MgO, NiO | $1^{st}$: 1300° C., 12 hr; $2^{nd}$: 1300° C., 12 hr |
| $Ca_{0.5}La_{0.5}Al_{11.5}Mn_{0.5}O_{19}$ | saddle brown | $CaCO_3$, $La_2O_3$, $Al_2O_3$, MnO | $1^{st}$: 1300° C., 12 hr; $2^{nd}$: 1400° C., 12 hr |
| $Ca_{0.9}Ce_{0.1}Al_{11.9}Ni_{0.1}O_{19}$ | Light Sky Blue | $CaCO_3$, $CeO_2$, $Al_2O_3$, NiO | $1^{st}$: 1300° C., 12 hr; $2^{nd}$: 1450° C., 12 hr |
| $Ca_{0.8}Ce_{0.2}Al_{11.8}Ni_{0.2}O_{19}$ | Sky Blue | $CaCO_3$, $CeO_2$, $Al_2O_3$, NiO | $1^{st}$: 1300° C., 12 hr; $2^{nd}$: 1450° C., 12 hr |
| $Ca_{0.7}Ce_{0.3}Al_{11.7}Ni_{0.3}O_{19}$ | Sky Blue | $CaCO_3$, $CeO_2$, $Al_2O_3$, NiO | $1^{st}$: 1300° C., 12 hr; $2^{nd}$: 1450° C., 12 hr |
| $Ca_{0.6}Ce_{0.4}Al_{11.6}Ni_{0.4}O_{19}$ | Sky Blue | $CaCO_3$, $CeO_2$, $Al_2O_3$, NiO | $1^{st}$: 1300° C., 12 hr; $2^{nd}$: 1450° C., 12 hr |
| $Ca_{0.5}Ce_{0.5}Al_{11.5}Ni_{0.5}O_{19}$ | Sky Blue | $CaCO_3$, $CeO_2$, $Al_2O_3$, NiO | $1^{st}$: 1300° C., 12 hr; $2^{nd}$: 1400° C., 12 hr |
| $Ca_{0.4}Ce_{0.6}Al_{11.4}Ni_{0.6}O_{19}$ | Sky Blue | $CaCO_3$, $CeO_2$, $Al_2O_3$, NiO | $1^{st}$: 1300° C., 12 hr; $2^{nd}$: 1400° C., 12 hr |
| $Ca_{0.3}Ce_{0.7}Al_{11.3}Ni_{0.7}O_{19}$ | Sky Blue | $CaCO_3$, $CeO_2$, $Al_2O_3$, NiO | $1^{st}$: 1300° C., 12 hr; $2^{nd}$: 1350° C., 12 hr |
| $Ca_{0.2}Ce_{0.8}Al_{11.2}Ni_{0.8}O_{19}$ | Sky Blue | $CaCO_3$, $CeO_2$, $Al_2O_3$, NiO | $1^{st}$: 1300° C., 12 hr; $2^{nd}$: 1350° C., 12 hr |
| $Ca_{0.1}Ce_{0.9}Al_{11.1}Ni_{0.9}O_{19}$ | Sky Blue | $CaCO_3$, $CeO_2$, $Al_2O_3$, NiO | $1^{st}$: 1300° C., 12 hr; $2^{nd}$: 1300° C., 12 hr |
| $CeAl_{11}NiO_{19}$ | Sky Blue | $CeO_2$, $Al_2O_3$, NiO | $1^{st}$: 1300° C., 12 hr; $2^{nd}$: 1300° C., 12 hr |
| $Ca_{0.9}Pr_{0.1}Al_{11.9}Ni_{0.1}O_{19}$ | Light Sky Blue | $CaCO_3$, $Pr_6O_{11}$, $Al_2O_3$, NiO | $1^{st}$: 1300° C., 12 hr; $2^{nd}$: 1450° C., 12 hr |
| $Ca_{0.8}Pr_{0.2}Al_{11.8}Ni_{0.2}O_{19}$ | Sky Blue | $CaCO_3$, $Pr_6O_{11}$, $Al_2O_3$, NiO | $1^{st}$: 1300° C., 12 hr; $2^{nd}$: 1450° C., 12 hr |
| $Ca_{0.7}Pr_{0.3}Al_{11.7}Ni_{0.3}O_{19}$ | Sky Blue | $CaCO_3$, $Pr_6O_{11}$, $Al_2O_3$, NiO | $1^{st}$: 1300° C., 12 hr; $2^{nd}$: 1450° C., 12 hr |
| $Ca_{0.6}Pr_{0.4}Al_{11.6}Ni_{0.4}O_{19}$ | Sky Blue | $CaCO_3$, $Pr_6O_{11}$, $Al_2O_3$, NiO | $1^{st}$: 1300° C., 12 hr; $2^{nd}$: 1450° C., 12 hr |
| $Ca_{0.5}Pr_{0.5}Al_{11.5}Ni_{0.5}O_{19}$ | Sky Blue | $CaCO_3$, $Pr_6O_{11}$, $Al_2O_3$, NiO | $1^{st}$: 1300° C., 12 hr; $2^{nd}$: 1400° C., 12 hr |
| $Ca_{0.4}Pr_{0.6}Al_{11.4}Ni_{0.6}O_{19}$ | Sky Blue | $CaCO_3$, $Pr_6O_{11}$, $Al_2O_3$, NiO | $1^{st}$: 1300° C., 12 hr; $2^{nd}$: 1400° C., 12 hr |
| $Ca_{0.3}Pr_{0.7}Al_{11.3}Ni_{0.7}O_{19}$ | Sky Blue | $CaCO_3$, $Pr_6O_{11}$, $Al_2O_3$, NiO | $1^{st}$: 1300° C., 12 hr; $2^{nd}$: 1350° C., 12 hr |
| $Ca_{0.2}Pr_{0.8}Al_{11.2}Ni_{0.8}O_{19}$ | Sky Blue | $CaCO_3$, $Pr_6O_{11}$, $Al_2O_3$, NiO | $1^{st}$: 1300° C., 12 hr; $2^{nd}$: 1350° C., 12 hr |
| $Ca_{0.1}Pr_{0.9}Al_{11.1}Ni_{0.9}O_{19}$ | Sky Blue | $CaCO_3$, $Pr_6O_{11}$, $Al_2O_3$, NiO | $1^{st}$: 1300° C., 12 hr; $2^{nd}$: 1300° C., 12 hr |
| $PrAl_{11}NiO_{19}$ | Sky Blue | $Pr_6O_{11}$, $Al_2O_3$, NiO | $1^{st}$: 1300° C., 12 hr; $2^{nd}$: 1300° C., 12 hr |
| $Ca_{0.9}Nd_{0.1}Al_{11.9}Ni_{0.1}O_{19}$ | Light Sky Blue | $CaCO_3$, $Nd_2O_3$, $Al_2O_3$, NiO | $1^{st}$: 1300° C., 12 hr; $2^{nd}$: 1450° C., 12 hr |
| $Ca_{0.8}Nd_{0.2}Al_{11.8}Ni_{0.2}O_{19}$ | Sky Blue | $CaCO_3$, $Nd_2O_3$, $Al_2O_3$, NiO | $1^{st}$: 1300° C., 12 hr; $2^{nd}$: 1450° C., 12 hr |
| $Ca_{0.7}Nd_{0.3}Al_{11.7}Ni_{0.3}O_{19}$ | Sky Blue | $CaCO_3$, $Nd_2O_3$, $Al_2O_3$, NiO | $1^{st}$: 1300° C., 12 hr; $2^{nd}$: 1450° C., 12 hr |
| $Ca_{0.6}Nd_{0.4}Al_{11.6}Ni_{0.4}O_{19}$ | Sky Blue | $CaCO_3$, $Nd_2O_3$, $Al_2O_3$, NiO | $1^{st}$: 1300° C., 12 hr; $2^{nd}$: 1450° C., 12 hr |
| $Ca_{0.5}Nd_{0.5}Al_{11.5}Ni_{0.5}O_{19}$ | Sky Blue | $CaCO_3$, $Nd_2O_3$, $Al_2O_3$, NiO | $1^{st}$: 1300° C., 12 hr; $2^{nd}$: 1400° C., 12 hr |
| $Ca_{0.4}Nd_{0.6}Al_{11.4}Ni_{0.6}O_{19}$ | Sky Blue | $CaCO_3$, $Nd_2O_3$, $Al_2O_3$, NiO | $1^{st}$: 1300° C., 12 hr; $2^{nd}$: 1400° C., 12 hr |
| $Ca_{0.3}Nd_{0.7}Al_{11.3}Ni_{0.7}O_{19}$ | Sky Blue | $CaCO_3$, $Nd_2O_3$, $Al_2O_3$, NiO | $1^{st}$: 1300° C., 12 hr; $2^{nd}$: 1350° C., 12 hr |
| $Ca_{0.2}Nd_{0.8}Al_{11.2}Ni_{0.8}O_{19}$ | Sky Blue | $CaCO_3$, $Nd_2O_3$, $Al_2O_3$, NiO | $1^{st}$: 1300° C., 12 hr; $2^{nd}$: 1350° C., 12 hr |
| $Ca_{0.1}Nd_{0.9}Al_{11.1}Ni_{0.9}O_{19}$ | Sky Blue | $CaCO_3$, $Nd_2O_3$, $Al_2O_3$, NiO | $1^{st}$: 1300° C., 12 hr; $2^{nd}$: 1300° C., 12 hr |
| $NdAl_{11}NiO_{19}$ | Sky Blue | $Nd_2O_3$, $Al_2O_3$, NiO | $1^{st}$: 1300° C., 12 hr; $2^{nd}$: 1300° C., 12 hr |

TABLE 1-continued

Composition, color and structures of exemplary compounds

| Composition | Color | Starting Materials | Heating Temperatures and Times |
|---|---|---|---|
| $CaAl_{11.4}Nb_{0.2}Ni_{0.4}O_{19}$ | Deep sky blue | $CaCO_3$, $Nb_2O_5$, $Al_2O_3$, NiO | $1^{st}$: 1300° C., 12 hr; $2^{nd}$: 1450° C., 12 hr |
| $CaAl_{11.4}Ta_{0.2}Ni_{0.4}O_{19}$ | Deep sky blue | $CaCO_3$, $Ta_2O_5$, $Al_2O_3$, NiO | $1^{st}$: 1300° C., 12 hr; $2^{nd}$: 1450° C., 12 hr |
| $CaAl_{11.4}V_{0.2}Ni_{0.4}O_{19}$ | Turquoise | $CaCO_3$, $V_2O_5$, $Al_2O_3$, NiO | $1^{st}$: 1300° C., 12 hr; $2^{nd}$: 1450° C., 12 hr |
| $CaAl_{11.4}Sb_{0.2}Ni_{0.4}O_{19}$ | Sky blue | $CaCO_3$, $Sb_2O_3$, $Al_2O_3$, NiO | $1^{st}$: 1300° C., 12 hr; $2^{nd}$: 1450° C., 12 hr |
| $CaAl_{11}Zr_{0.5}Ni_{0.5}O_{19}$ | Light sky blue | $CaCO_3$, $ZrO_2$, $Al_2O_3$, NiO | $1^{st}$: 1300° C., 12 hr; $2^{nd}$: 1450° C., 12 hr |
| $CaAl_{11}Te_{0.5}Ni_{0.5}O_{19}$ | Very light sky blue | $CaCO_3$, $TeO_2$, $Al_2O_3$, NiO | $1^{st}$: 1300° C., 12 hr; $2^{nd}$: 1450° C., 12 hr |

Figure 3:
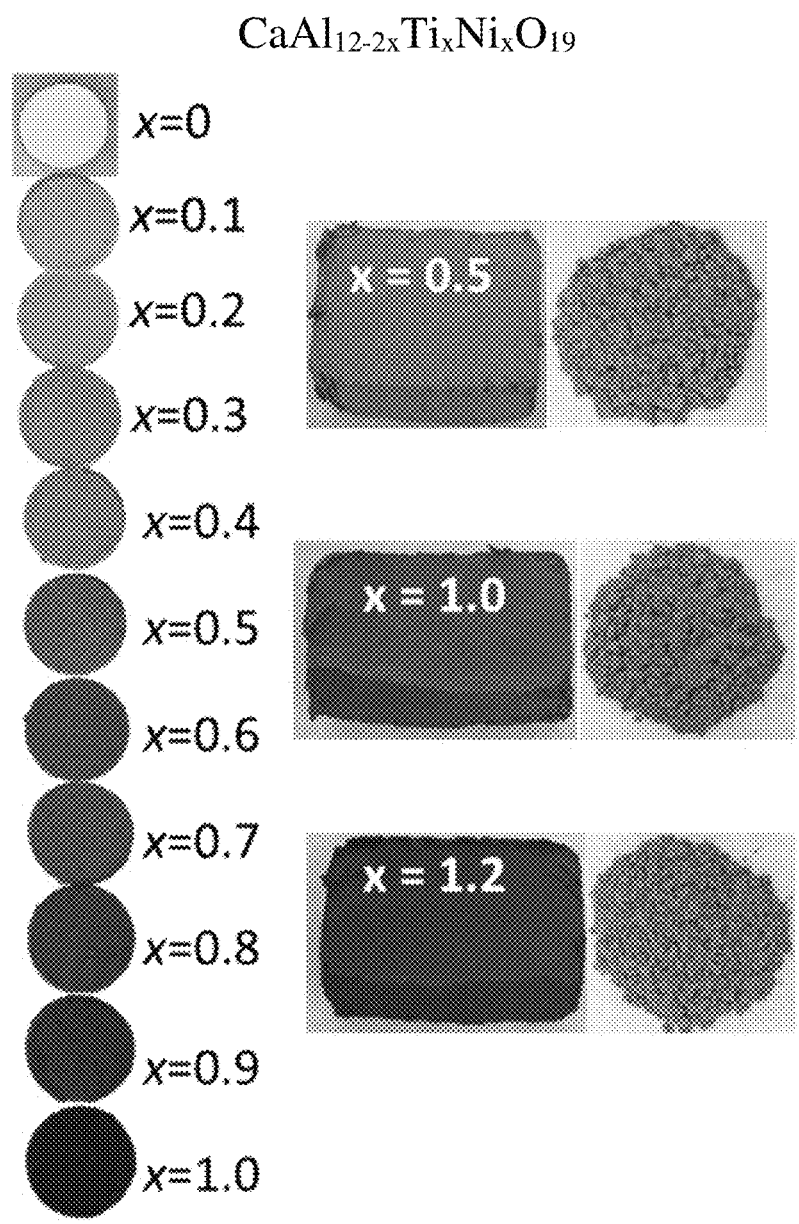
FIG. 3 provides a series of color photographs of blue pellets and powders of $CaAl_{12-2x}Ti_xNi_xO_{19}$ (x=0-1.2) demonstrating that color can be selected by the appropriate selection of metals and their relative amounts.

The colors can be varied or selected by changing the relative ratio of metals in the compound, or by changing the composition. FIG. 3 shows the results of varying the relative ratio of metals in an exemplary series of compounds, $CaAl_{12-2x}Ti_xNi_xO_{19}$ (x=0-1.2). In this series, the compound when x is 0, i.e. no Ti or Ni present, has a white color. The introduction of Ti and Ni (x=0.1) results in a blue compound. As compounds with increasing amounts of Ti and Ni are synthesized, the colors of the compounds change from a light sky blue at x=0.1 ($CaAl_{11.8}Ti_{0.1}Ni_{0.1}O_{19}$), through a deep sky blue at x=1.0 ($CaAl_{10}TiNiO_{19}$), to a royal blue color at x=1.2 ($CaAl_{9.6}Ti_{1.2}Ni_{1.2}O_{19}$). Surprisingly, the color of the pellet is substantially maintained when the pellet is ground to a powder, thereby making the compound suitable for use as a pigment (FIG. 3).

FIG. 4 shows the results of varying the composition of the compounds. In the series of compounds having a formula $CaAl_{12-x-y}M_xNi_yO_{19}$ (x, y=0.2-0.5), where M is Ti, Sn, Ge, Sb or Nb, all the samples have a blue color. $CaAl_{11}Sn_{0.5}Ni_{0.5}O_{19}$ and $CaAl_{11.4}Sb_{0.2}Ni_{0.4}O_{19}$ have a light sky blue color, and $CaAl_{11}Ti_{0.5}Ni_{0.5}O_{19}$, $CaAl_{11}Ge_{0.5}Ni_{0.5}O_{19}$ and $CaAl_{11.4}Nb_{0.2}Ni_{0.4}O_{19}$ have a deep sky blue color.

III. Compositions

The present disclosure is also concerns compositions comprising at least one disclosed compound or compounds, particularly a hibonite compound, even more particularly a blue hibonite compound or a compound having formula II, and at least one additional component. Such compositions include a paint, an ink, a dye, a glass, a plastic, an emulsion, a fabric, or a cosmetic preparation. Suitable additional components for use in paint, ink dye or emulsion products include, but are not limited to, binders, solvents, and additives such as catalysts, thickeners, stabilizers, emulsifiers, texturizers, adhesion promoters, UV stabilizers, flatteners (i.e., de-glossing agents), preservatives, and other additives known to those of ordinary skill in the art.

Suitable additional materials for use in glass products include, for example, network formers (e.g., oxides of silicon, boron, germanium) to form a highly crosslinked network of chemical bonds, modifiers (e.g., calcium, lead, lithium, sodium, potassium) that alter the network structure, intermediates (e.g., titanium, aluminum, zirconium, beryllium, magnesium, zinc) that can act as both network formers and modifiers, and combinations thereof.

Suitable additional materials for use in plastic products include, for example, dispersion aids (e.g., zinc stearate, calcium stearate, ethylene bis-steamide), plasticizers, flame retardants, internal mold release agents, slip agents, and combinations thereof.

When coloring a ceramic product, the material typically is added to a ceramic glaze composition. Other materials used in glazes include, for example, silica, metal oxides (e.g., sodium, potassium, calcium), alumina, opacifiers (e.g., tin oxide, zirconium oxide), and combinations thereof.

IV. Working Examples

The compounds disclosed herein were prepared via traditional solid state reactions.

Amounts of metal carbonates and/or metal oxides were selected and weighed to provide the desired stoichiometric amounts of the metals. Typically, the alkali metals and alkaline earth metals were provided as metal carbonate salts, and the other metals were provided as metal oxides. The starting materials were then mixed, ground and pelletized, then heated in air at a range of from about 1,200° C. to about 1,500° C. several times with intermediate grinding. Ramp rates were about 300° C./hour. Table 1, above, gives the starting metal salts and oxides for each exemplary compound, and the heating temperatures and times for each heating cycle. For example, $CaCO_3$ (0.0721 grams, 1 molar equivalent), $Al_2O_3$ (0.4039 grams, 5.5 molar equivalents), $TiO_2$ (0.0288 grams, 0.5 molar equivalents) and NiO (0.0269 grams, 0.5 molar equivalents) were weighed, mixed/ground, pelletized and heated in air at 1,300° C. for 12 hours, then ground to a powder, re-pelletized and reheated at 1,400° C. for 12 hours to prepare 0.5g of $CaAl_{11}Ti_{0.5}Ni_{0.5}O_{19}$.

Figure 5:
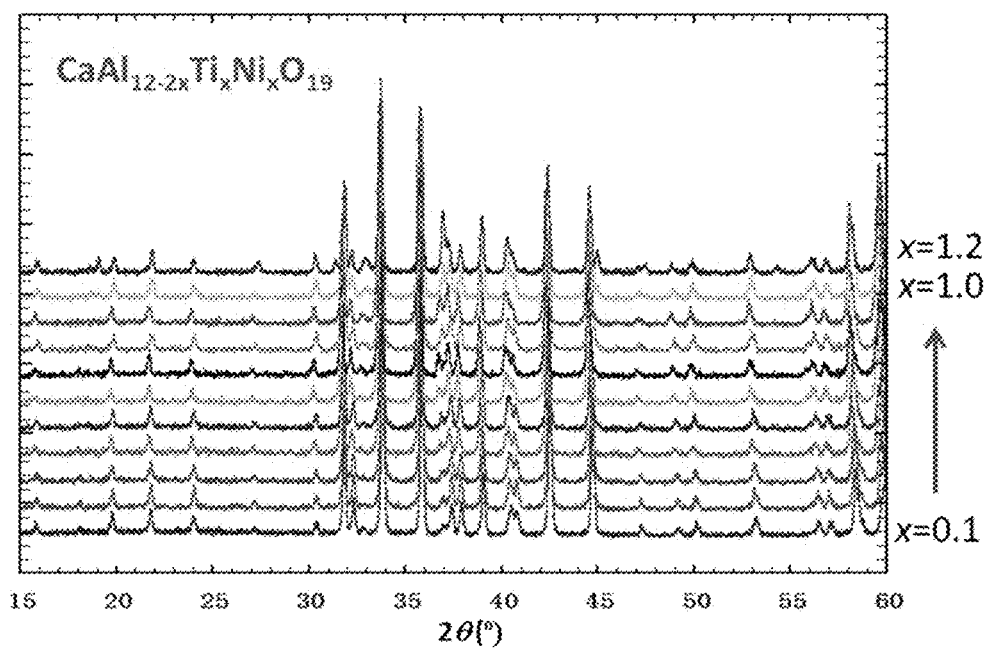
FIG. 5 provides a series of X-ray powder diffraction patterns for $CaAl_{12-2x}Ti_xNi_xO_{19}$ (x=0-1.2) solid solutions.
Figure 6:
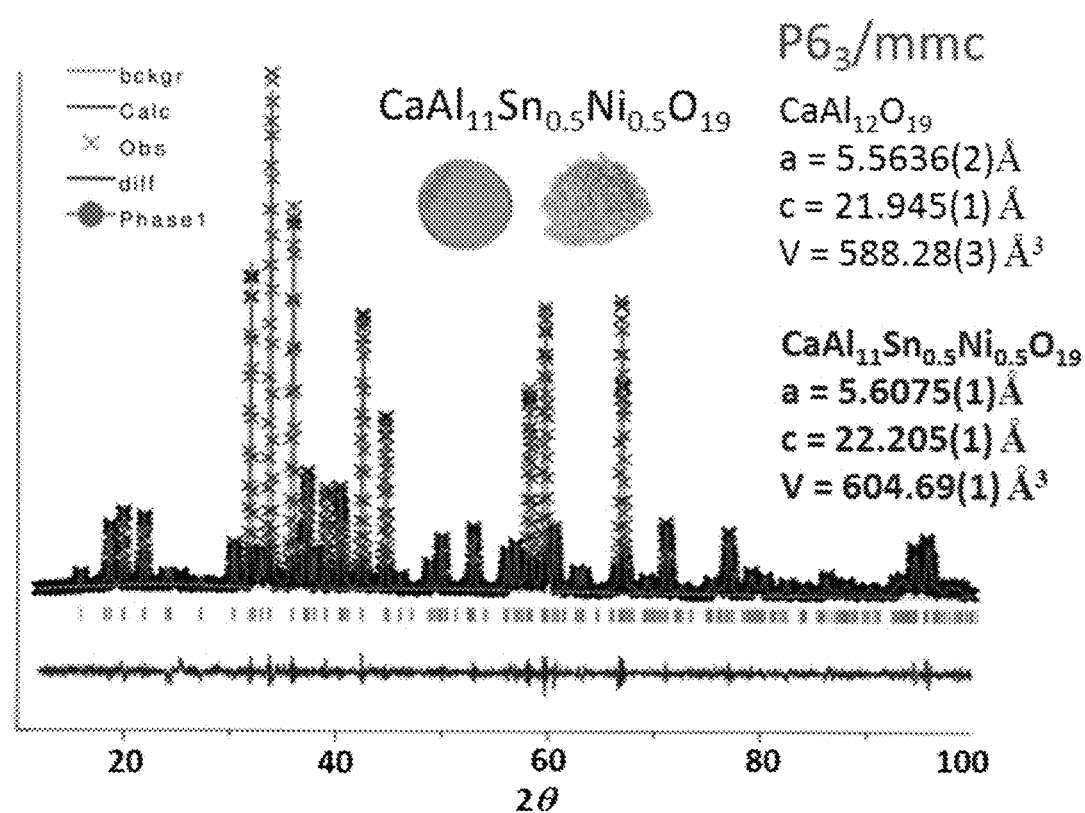
FIG. 6 provides the results of cell edge calculations by whole pattern fitting for $CaAl11Sn_{0.5}Ni_{0.5}O_{19}$.
Figure 7:
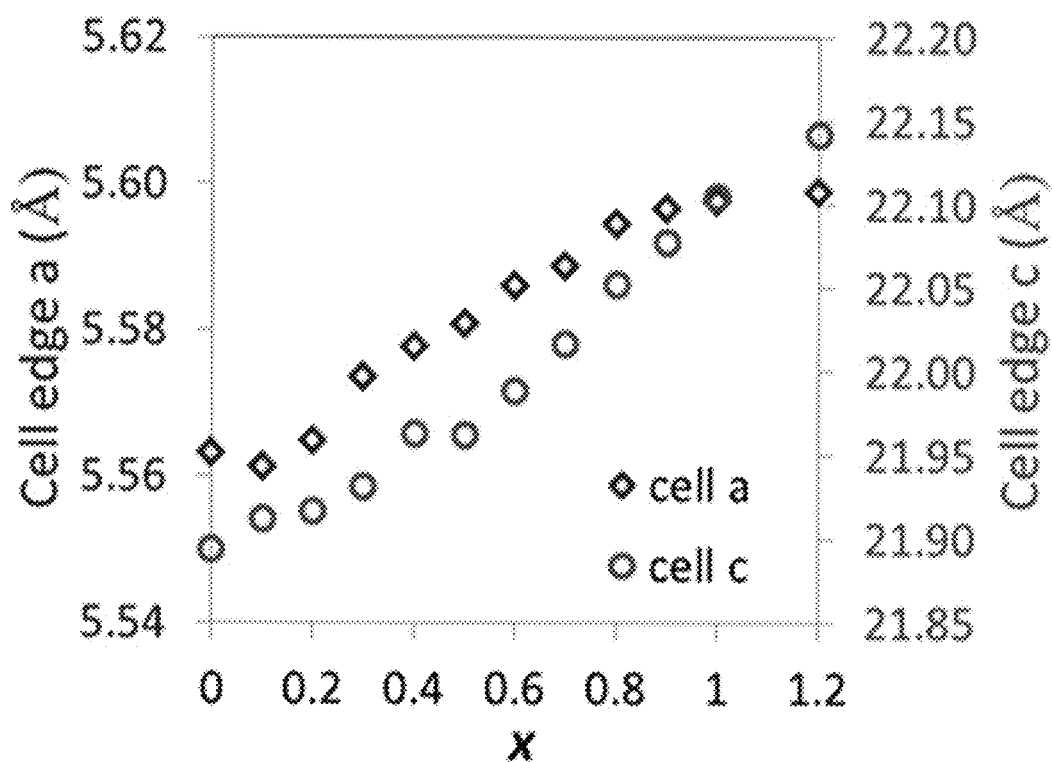
FIG. 7 provides unit cell dimensions in angstroms (Å) for cell edges 'a' and 'c' for solid solutions of $CaAl_{12-2x}Ti_xNi_xO_{19}$ (x=0-1.2), illustrating that as the composition changes, the dimensions of the crystal vary correspondingly.
Figure 8:
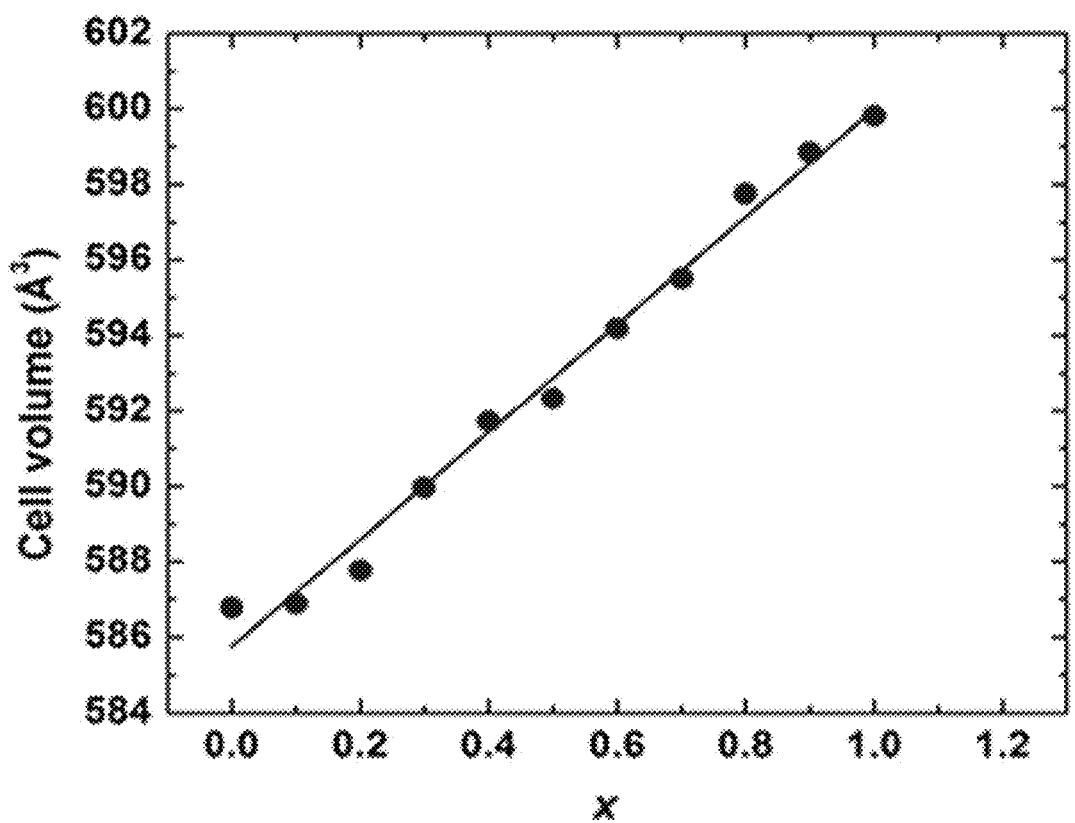
FIG. 8 provides unit cell volumes in cubic angstroms ($Å^3$) for solid solutions of $CaAl_{12-2x}Ti_xNi_xO_{19}$ (x=0-1.2), illustrating that the unit cell volume varies correspondingly with the changes to the composition.

X-ray diffraction patterns of exemplary solid solutions of $CaAl_{12-2x}Ti_xNi_xO_{19}$ (x=0.1-1.2) are shown in FIG. 5. The X-ray diffraction data was obtained using a Rigaku Miniflex X-ray diffractometer using Cu $K\alpha$ radiation and a graphite monochromator. The lattice parameters of the unit cells were calculated by whole pattern fitting as shown in FIG. 6, using the data of $CaAl_{11}Sn_{0.5}Ni_{0.5}O_{19}$ as an example. The results indicate that cell edge 'a' was 5.6075 Å, 'c' was 22.205 Å and the cell volume was 604.69 Å$^3$. In comparison, for $CaAl_{12}O_{19}$ cell edge 'a' was 5.5636 Å, 'c' was 21.945 Å and the cell volume was 588.28 Å$^3$. The increase of hibonite unit cell volume was consistent with the substitution of small $Al^{3+}$ ions with larger $Ni^{2+}$, $Ti^{4+}$ and $La^{3+}$ ions (FIGS. 7 and 8).

Diffuse reflectance spectra of powdered samples were obtained in the region 300-1100nm using a Xe lamp and a grating double monochromator as the source. The diffuse light reflected by the powders was collected with an integration sphere and detected with a Si diode detector. MgO was used as a reference. The data were transformed into absorbance using the Kubelka-Munk function.

Figure 9:
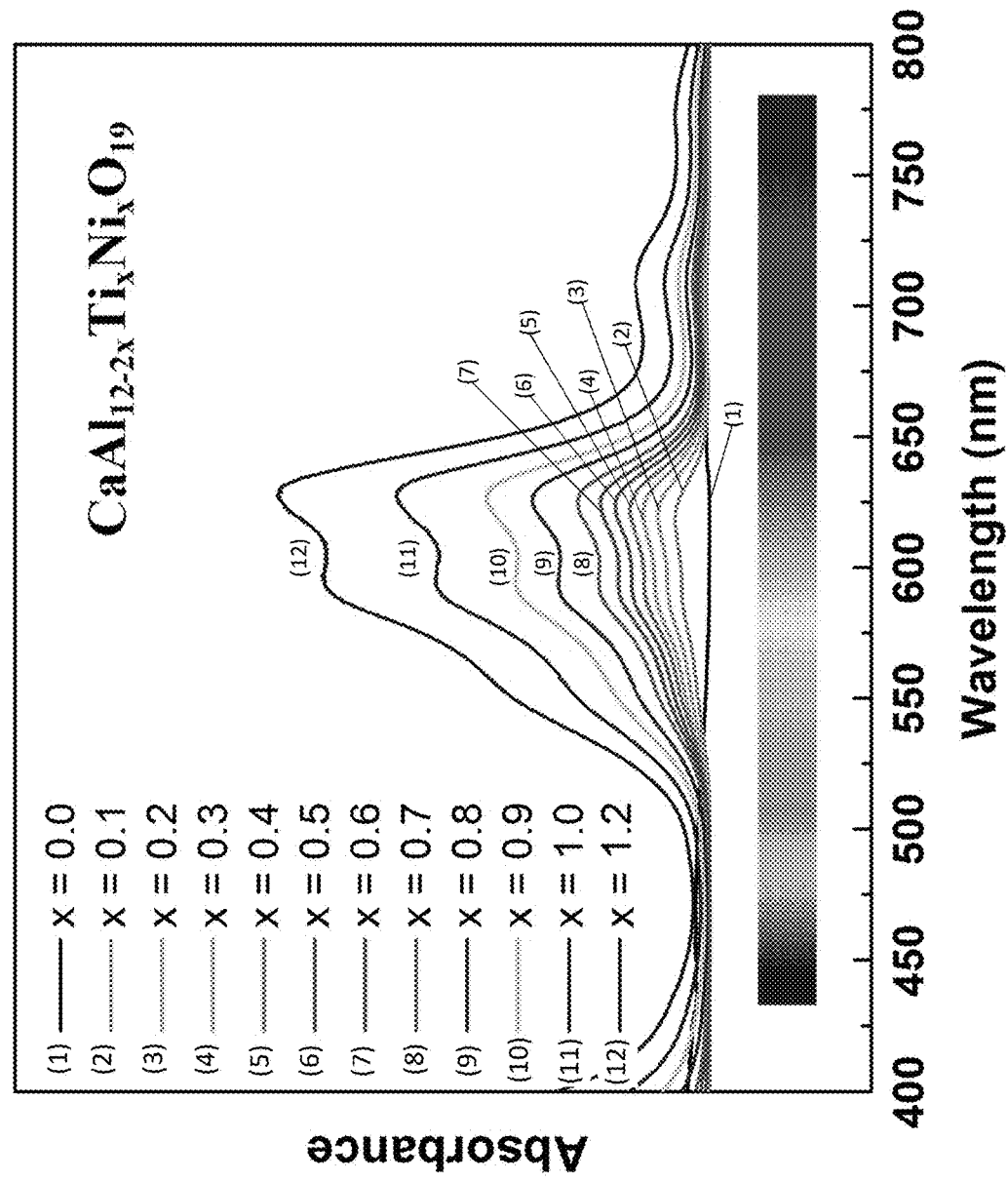
FIG. 9 provides a series of diffuse reflectance spectra for $CaAl_{12-2x}Ti_xNi_xO19$ (x=0-1.2) solid solutions, indicating that as x increases absorbance of light with wavelengths in the blue region of the spectrum remains low, but absorbance in other regions of the spectrum increases, resulting in blue colored compounds.

The 400-800 nm region of diffuse reflectance spectra for solid solution of exemplary compounds $CaAl_{12-2x}Ti_xNi_xO_{19}$ (x=0-1.2) are shown in FIG. 9. Strong absorption in the orange spectral region combined with relatively weak absorption in the blue region was responsible for the observed bright blue color. In pure $CaAl_{12}O_{19}$ (i.e. x=0), nearly no absorption occurs throughout the entire visible region, resulting in the white color. With increasing Ni composition, the onset of the first absorption peak shifts to lower energy and the second broadens, consistent with the gradual darkening of the samples toward royal blue.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula $AAl_{12-x-y}M^a_xM^b_yO_{19}$, wherein:
   A is selected from Ca, Sr, Ba, Mg, Sc, Y, La, Ce, Pr, Nd, Sm, Eu, Gd, Tb, Dy, Ho, Er, Tm, Yb, Lu, Li, Na, K, Rb, Cs, Pb, Bi or any combination thereof;
   $M^a$ is selected from Ni, Fe, Cu, Cr, V, Mn, or Co or any combination thereof;
   $M^b$ is selected from Ti, Sn, Ge, Si, Zr, Hf, Ga, In, Zn, Mg, Nb, Ta, Sb, Mo, W or Te or any combination thereof;
   x is from 0.01 to less than 12;
   y is from 0 to less than 12;
   x+y is less than 12; and
   if y is 0, then x is from 0.01 to less than 1;
   if $M^a$ comprises Fe, then y is greater than 0, or $M^a$ further comprises Ni, Cu, Cr, V, Mn, or Co or any combination thereof; and
   if $M^a$ is Mn and $M^b$ is Mg, then x+y is less than 1, or x+y is greater than 1.

2. The compound of claim 1, wherein x is from 0.01 to less than 12 and y is from 0.01 to less than 12.

3. The compound of claim 1, wherein:
   A is $A^1_{1-z}A^2_z$;
   $A^1$ is selected from Ca, Sr, Ba, Mg, Sc, Y, Li, Na, K, Rb, Cs, Pb, Bi or any combination thereof;
   $A^2$ is selected from La, Ce, Pr, Nd, Sm, Eu, Gd, Tb, Dy, Ho, Er, Tm, Yb, Lu or any combination thereof; and
   z is from 0 to less than 1.

4. The compound of claim 1, wherein the compound is selected from $CaAl_{11.8}Ni_{0.2}O_{19}$, $CaAl_{11.5}Ni_{0.5}O_{19}$, $CaAl_{11}Sn_{0.5}Ni_{0.5}O_{19}$, $CaAl_{10}SnNiO_{19}$, $CaAl_{11}Zn_{0.5}Ni_{0.5}O_{19}$, $CaAl_{11}Ge_{0.5}Ni_{0.5}O_{19}$, $CaAl_{10}GeNiO_{19}$, $CaAl_{11}Ga_{0.5}Ni_{0.5}O_{19}$, $CaAl_{11}Ti_{0.5}Ni_{0.5}O_{19}$, $CaAl_{10}Ti_{0.5}Si_{0.5}NiO_{19}$, $CaAl_{10}Ti_{0.5}Ge_{0.5}NiO_{19}$, $CaAl_{10}Ti_{0.5}Sn_{0.5}NiO_{19}$, $CaAl_8TiSnNi_2O_{19}$, $CaAl_{10}TiNi_{0.5}Cu_{0.5}O_{19}$, $CaAl_{10}TiNi_{0.5}Cr_{0.5}O_{19}$, $CaAl_{10}TiNi_{0.5}Zn_{0.5}O_{19}$, $CaAl_{11.8}Ti_{0.1}Ni_{0.1}O_{19}$, $CaAl_{11.6}Ti_{0.2}Ni_{0.2}O_{19}$, $CaAl_{11.4}Ti_{0.3}Ni_{0.3}O_{19}$, $CaAl_{11.2}Ti_{0.4}Ni_{0.4}O_{19}$, $CaAl_{11}Ti_{0.5}Ni_{0.5}O_{19}$, $CaAl_{10.8}Ti_{0.6}Ni_{0.6}O_{19}$, $CaAl_{10.6}Ti_{0.7}Ni_{0.7}O_{19}$, $CaAl_{10.4}Ti_{0.8}Ni_{0.8}O_{19}$, $CaAl_{10.2}Ti_{0.9}Ni_{0.9}O_{19}$, $CaAl_{10}TiNiO_{19}$, $CaAl_{9.6}Ti_{1.2}Ni_{1.2}O_{19}$, $CaAl_8Ti_2Ni_2O_{19}$, $Ca_{0.8}Sr_{0.2}Al_{11.6}Ti_{0.2}Ni_{0.2}O_{19}$, $Ca_{0.6}Sr_{0.4}Al_{11.2}Ti_{0.4}Ni_{0.4}O_{19}$, $Ca_{0.4}Sr_{0.6}Al_{10.8}Ti_{0.6}Ni_{0.6}O_{19}$, $Ca_{0.2}Sr_{0.8}Al_{10.4}Ti_{0.8}Ni_{0.8}O_{19}$, $SrAl_{10}TiNiO_{19}$, $SrAl_{9.6}Ti_{1.2}Ni_{1.2}O_{19}$, $SrAl_{11}Ti_{0.5}Ni_{0.5}O_{19}$, $SrAl_8Ti_2Ni_2O_{19}$, $Ca_{0.5}Sr_{0.5}Al_8Ti_2Ni_2O_{19}$, $Ca_{0.5}Sr_{0.5}Al_{10}TiNiO_{19}$, $Ca_{0.5}Sr_{0.5}Al_{10}GeNiO_{19}$, $Ca_{0.5}Sr_{0.5}Al_{11}Sn_{0.5}Ni_{0.5}O_{19}$, $Ca_{0.5}Sr_{0.5}Al_{10}SnNiO_{19}$, $Sr_{0.9}La_{0.1}Al_{11.9}Ni_{0.1}O_{19}$, $Sr_{0.8}La_{0.2}Al_{11.8}Ni_{0.2}O_{19}$, $Sr_{0.7}La_{0.3}Al_{11.7}Ni_{0.3}O_{19}$, $Sr_{0.6}La_{0.4}Al_{11.6}Ni_{0.4}O_{19}$, $Sr_{0.5}La_{0.5}Al_{11.5}Ni_{0.5}O_{19}$, $Sr_{0.4}La_{0.6}Al_{11.4}Ni_{0.6}O_{19}$, $Sr_{0.3}La_{0.7}Al_{11.3}Ni_{0.7}O_{19}$, $Sr_{0.2}La_{0.8}Al_{11.2}Ni_{0.8}O_{19}$, $Sr_{0.1}La_{0.9}Al_{11.1}Ni_{0.9}O_{19}$, $Ca_{0.9}La_{0.1}Al_{11.9}Ni_{0.1}O_{19}$, $Ca_{0.8}La_{0.2}Al_{11.8}Ni_{0.2}O_{19}$, $Ca_{0.7}La_{0.3}Al_{11.7}Ni_{0.3}O_{19}$, $Ca_{0.6}La_{0.4}Al_{11.6}Ni_{0.4}O_{19}$, $Ca_{0.5}La_{0.5}Al_{11.5}Ni_{0.5}O_{19}$, $Ca_{0.4}La_{0.6}Al_{11.4}Ni_{0.6}O_{19}$, $Ca_{0.3}La_{0.7}Al_{11.3}Ni_{0.7}O_{19}$, $Ca_{0.2}La_{0.8}Al_{11.2}Ni_{0.8}O_{19}$, $Ca_{0.1}La_{0.9}Al_{11.1}Ni_{0.9}O_{19}$, $Ca_{0.75}La_{0.25}Al_{11.25}Ti_{0.25}Ni_{0.5}O_{19}$, $Ca_{0.5}La_{0.5}Al_{11}Ti_{0.25}Ni_{0.75}O_{19}$, $Ca_{0.25}La_{0.75}Al_{9.75}Ti_{0.75}Ni_{1.5}O_{19}$, $Ca_{0.5}La_{0.5}Al_{10.5}Ti_{0.5}NiO_{19}$, $Ca_{0.5}La_{0.5}Al_{8.5}Ti_{1.5}Ni_2O_{19}$, $LaAl_9TiNi_2O_{19}$, $Ca_{0.5}La_{0.5}Al_{11}In_{0.5}Ni_{0.5}O_{19}$, $Ca_{0.5}La_{0.5}Al_{11}Ga_{0.5}Ni_{0.5}O_{19}$, $Ca_{0.5}La_{0.5}Al_{11}Ge_{0.25}Ni_{0.75}O_{19}$, $Ca_{0.5}La_{0.5}Al_{11}Sn_{0.25}Ni_{0.75}O_{19}$, $Ca_{0.75}La_{0.25}Al_{11.75}Ni_{0.25}O_{19}$, $Ca_{0.5}Y_{0.5}Al_{11}Ti_{0.25}Ni_{0.75}O_{19}$, $Ca_{0.5}Ce_{0.5}Al_{11}Ti_{0.25}Ni_{0.75}O_{19}$, $Ca_{0.5}Pr_{0.5}Al_{11}Ti_{0.25}Ni_{0.75}O_{19}$, $Ca_{0.5}Na_{0.5}Al_{10.5}TiNi_{0.5}O_{19}$, $Ca_{0.5}K_{0.5}Al_{10.5}TiNi_{0.5}O_{19}$, $Ca_{0.5}Rb_{0.5}Al_{10.5}TiNi_{0.5}O_{19}$, $Ca_{0.5}Cs_{0.5}Al_{10.5}TiNi_{0.5}O_{19}$, $Ca_{0.8}Mg_{0.2}Al_{11.6}Ti_{0.2}Ni_{0.2}O_{19}$, $Ca_{0.5}Ba_{0.5}Al_8Ti_2Ni_2O_{19}$, $Sr_{0.9}Y_{0.1}Al_{11.9}Ni_{0.1}O_{19}$, $Sr_{0.8}Y_{0.2}Al_{11.8}Ni_{0.2}O_{19}$, $Sr_{0.8}Ce_{0.2}Al_{11.8}Ni_{0.2}O_{19}$, $Sr_{0.8}Nd_{0.2}Al_{11.8}Ni_{0.2}O_{19}$, $Sr_{0.8}Pr_{0.2}Al_{11.8}Ni_{0.2}O_{19}$, $Ca_{0.9}Y_{0.1}Al_{11.9}Ni_{0.1}O_{19}$, $Ca_{0.8}Y_{0.2}Al_{11.8}Ni_{0.2}O_{19}$, $Ca_{0.7}Y_{0.3}Al_{11.7}Ni_{0.3}O_{19}$, $Ca_{0.6}Y_{0.4}Al_{11.6}Ni_{0.4}O_{19}$, $Ca_{0.5}La_{0.5}Al_{10.5}Zn_{0.5}Sn_{0.5}Ni_{0.5}O_{19}$, $Ca_{0.5}La_{0.5}Al_{10.5}Cu_{0.5}Sn_{0.5}Ni_{0.5}O_{19}$, $Ca_{0.8}Sc_{0.2}Al_{11.8}Ni_{0.2}O_{19}$, $Ca_{0.8}Yb_{0.2}Al_{11.8}Ni_{0.2}O_{19}$, $Ca_{0.7}Sr_{0.3}Al_{11.5}Ni_{0.5}O_{19}$, $CaAl_7Ti_{1.5}Ge_{0.5}MgNi_2O_{19}$, $Ca_{0.9}Ce_{0.1}Al_{11.9}Ni_{0.1}O_{19}$, $Ca_{0.8}Ce_{0.2}Al_{11.8}Ni_{0.2}O_{19}$, $Ca_{0.7}Ce_{0.3}Al_{11.7}Ni_{0.3}O_{19}$, $Ca_{0.6}Ce_{0.4}Al_{11.6}Ni_{0.4}O_{19}$, $Ca_{0.5}Ce_{0.5}Al_{11.5}Ni_{0.5}O_{19}$, $Ca_{0.4}Ce_{0.6}Al_{11.4}Ni_{0.6}O_{19}$, $Ca_{0.3}Ce_{0.7}Al_{11.3}Ni_{0.7}O_{19}$, $Ca_{0.2}Ce_{0.8}Al_{11.2}Ni_{0.8}O_{19}$, $Ca_{0.1}Ce_{0.9}Al_{11.1}Ni_{0.9}O_{19}$, $Ca_{0.9}Pr_{0.1}Al_{11.9}Ni_{0.1}O_{19}$, $Ca_{0.8}Pr_{0.2}Al_{11.8}Ni_{0.2}O_{19}$, $Ca_{0.7}Pr_{0.3}Al_{11.7}Ni_{0.3}O_{19}$, $Ca_{0.6}Pr_{0.4}Al_{11.6}Ni_{0.4}O_{19}$, $Ca_{0.5}Pr_{0.5}Al_{11.5}Ni_{0.5}O_{19}$, $Ca_{0.4}Pr_{0.6}Al_{11.4}Ni_{0.6}O_{19}$, $Ca_{0.3}Pr_{0.7}Al_{11.3}Ni_{0.7}O_{19}$, $Ca_{0.2}Pr_{0.8}Al_{11.2}Ni_{0.8}O_{19}$, $Ca_{0.1}Pr_{0.9}Al_{11.1}Ni_{0.9}O_{19}$, $Ca_{0.9}Nd_{0.1}Al_{11.9}Ni_{0.1}O_{19}$, $Ca_{0.8}Nd_{0.2}Al_{11.8}Ni_{0.2}O_{19}$, $Ca_{0.7}Nd_{0.3}Al_{11.7}Ni_{0.3}O_{19}$, $Ca_{0.6}Nd_{0.4}Al_{11.6}Ni_{0.4}O_{19}$, $Ca_{0.5}Nd_{0.5}Al_{11.5}Ni_{0.5}O_{19}$, $Ca_{0.4}Nd_{0.6}Al_{11.4}Ni_{0.6}O_{19}$, $Ca_{0.3}Nd_{0.7}Al_{11.3}Ni_{0.7}O_{19}$, $Ca_{0.2}Nd_{0.8}Al_{11.2}Ni_{0.8}O_{19}$, $Ca_{0.1}Nd_{0.9}Al_{11.1}Ni_{0.9}O_{19}$, $CaAl_{11.4}Nb_{0.2}Ni_{0.4}O_{19}$, $CaAl_{11.4}Ta_{0.2}Ni_{0.4}O_{19}$, $CaAl_{11.4}V_{0.2}Ni_{0.4}O_{19}$, $CaAl_{11.4}Sb_{0.2}Ni_{0.4}O_{19}$, $CaAl_{11}Zr_{0.5}Ni_{0.5}O_{19}$ or $CaAl_{11}Te_{0.5}Ni_{0.5}O_{19}$.

5. The compound of claim 1, wherein $M^a$ comprises Ni, Co or any combination thereof.

6. The compound of claim 1 wherein $M^a$ is Ni.

7. The compound of claim 1, wherein x+y is less than or equal to 4.

8. The compound of claim 1, wherein y is from 0 to 2.

9. The compound of claim 8, wherein x is from 0.01 to 2.

10. The compound of claim 1, wherein the compound has a blue color.

11. The compound of claim 10, wherein the blue color has a wavelength of from about 440 nm to about 510 nm.

12. The compound of claim 10, wherein the compound has a hibonite crystal structure.

13. The compound of claim 10, wherein $M^b$ comprises Ti.

14. The compound of claim 10, wherein A comprises Ca, La, Sr or any combination thereof.

15. The compound of claim 10, wherein $M^a$ is Co and x is from 0.05 to 1.5.

16. The compound of claim 10, wherein:
   $M^a$ is Ni;
   $M^b$ is selected from Ti, Ge, Sn or any combination thereof; and
   x is from 0.05 to 1.5.

17. The compound of claim 1, wherein $M^a$ comprises at least two metals selected from Ni, Cr, Cu, V, Mn, Co or Fe.

18. The compound of claim 1, wherein $M^a$ comprises V and at least one additional metal selected from Ni, Cr, Cu, Mn, Co or Fe.

19. The compound of claim 1, wherein $M^a$ comprises Cr and at least one additional metal selected from Ni, V, Cu, Mn, Co or Fe.

20. A composition, comprising:
   a compound of claim 1; and
   at least one additional component.

21. The composition of claim 20, wherein the composition is a paint, an ink, a dye, a glass, a plastic, an emulsion, a fabric, or a cosmetic preparation.

22. The composition of claim 20, wherein the at least one additional component is a binder, a solvent, a catalyst, a thickener, a stabilizer, an emulsifier, a texturizer, an adhesion promoter, a UV stabilizer, a flattener, a preservative, a polymer, a dispersion aid, a plasticizer, a flame retardant, an oxide of a metal, or any combination thereof.

23. The composition of claim 20, wherein the composition is a glass, and the at least one additional component is a metal oxide.

24. The composition of claim 20, further comprising at least one additional compound according to claim 1.

25. A method for making a compound of claim 1, the method comprising:
   selecting metals desired in the compound;
   providing reactants comprising the selected metals;
   combining the reactants in stoichiometric amounts to achieve a desired final ratio of the selected metals in the compound; and
   heating the combination of reactants at an effective temperature for an effective period of time to make the compound of claim 1.

* * * * *